US010443071B2

(12) United States Patent
Tomizawa

(10) Patent No.: US 10,443,071 B2
(45) Date of Patent: Oct. 15, 2019

(54) METHODS AND MATERIALS FOR OBTAINING HEPATOCYTE LINEAGE CELLS

(71) Applicant: National University Corporation Chiba University, Chiba (JP)

(72) Inventor: Minoru Tomizawa, Chiba (JP)

(73) Assignee: National University Corporation Chiba University, Chiba (JP)

(*) Notice: Subject to any disclaimer, the term of this patent is extended or adjusted under 35 U.S.C. 154(b) by 146 days.

(21) Appl. No.: 15/417,241

(22) Filed: Jan. 27, 2017

(65) Prior Publication Data

US 2017/0218394 A1 Aug. 3, 2017

Related U.S. Application Data

(60) Provisional application No. 62/288,516, filed on Jan. 29, 2016.

(51) Int. Cl.
*C12N 15/85* (2006.01)
*C12N 5/074* (2010.01)

(52) U.S. Cl.
CPC ........... *C12N 15/85* (2013.01); *C12N 5/0696* (2013.01); *C12N 2506/03* (2013.01); *C12N 2800/40* (2013.01); *C12N 2820/60* (2013.01)

(58) Field of Classification Search
CPC .................................................... C12N 15/85
See application file for complete search history.

(56) References Cited

PUBLICATIONS

Ishizaka et al. (2002, FASEB J., vol. 16(11), pp. 1-20) (Year: 2002).*
Snykers et al. (2009, Stem Cells, vol. 27, pp. 577-605) (Year: 2009).*
Sekiya et al. (2011, Nature, vol. 475, pp. 390-395). (Year: 2011).*
Bi et al. (2014, Cellular Physiology and Biochemistry, vol. 34, pp. 1318-1338). (Year: 2014).*
Dong et al. (2008, Cytotechnology, vol. 57, pp. 251-261). (Year: 2008).*
Takahashi et al. (2007, Cell, vol. 131, pp. 861-872). (Year: 2007).*
Grabowska et al. (2014, Mol. Endocrinol., vol. 28(6), pp. 949-964). (Year: 2014).*
Gaunitz et al. (1996, BioTechniques, vol. 20(5), pp. 826-830). (Year: 1996).*
Akira et al., "A nuclear factor for IL-6 expression (NF-IL6) is a member of a C/EBP family," The EMBO Journal, 1990, vol. 9, No. 6, pp. 1897-1906.
Antonson et al., "Molecular Cloning, Sequence, and Expression Patterns of the Human Gene Encoding CCAAT/Enhancer Binding Protein alpha (C/EBPalpha)," Biochemical and Biophysical Research Communications, 1995, vol. 215, No. 1, pp. 106-113.
Chang et al., "Improvement of Carbon Tetrachloride-Induced Acute Hepatic Failure by Transplantation of Induced Pluripotent Stem Cells without Reprogramming Factor c-Myc," International Journal of Molecular Sciences, 2012, vol. 13, pp. 3598-3617.
Costa et al., "Transcription Factors in Liver Development, Differentiation, and Regeneration," Hepatology, 2003, vol. 38, No. 6, pp. 1331-1347.
Dabos et al., "Comparison of Bioenergetic Activity of Primary Porcine Hepatocytes Cultured in Four Different Media," Cell Transplantation, 2004, vol. 13, pp. 213-229.
Delaforest et al., "HNF4A is essential for specification of hepatic progenitors from human pluripotent stem cells," Development, 2011, vol. 138, pp. 4143-4153.
Duan et al., "Differentiation and Characterization of Metabolically Functioning Hepatocytes from Human Embryonic Stem Cells," Stem Cells, 2010, vol. 28, pp. 674-686.
Farghali et al., "Urea Synthesis and Cyclosporin a Biotransformation in a Laboratory Scale-Hepatocyte Bioreactor Model," Pharmacological Research, 2002, vol. 46, No. 6, pp. 511-517.
Hang et al., "Induction of Highly Functional Hepatocytes from Human Umbilical Cord Mesenchymal Stem Cells by HNF4alpha Transduction," PLOS ONE, 2014, vol. 9, No. 8, e104133, pp. 1-9.
Hirschi et al., "Induced Pluripotent Stem Cells for Regenerative Medicine," Annu Rev Biomed Eng., 2014, vol. 16, pp. 277-294 (pp. 1-20).
Inamura et al., "Efficient Generation of Hepatoblasts From Human ES Cells and iPS Cells by Transient Overexpression of Homeobox Gene HEX," Molecular Therapy, 2011, vol. 19, No. 2, pp. 400-407.
Kheolamai et al., "Liver-enriched transcription factors are critical for the expression of hepatocyte marker genes in mES-derived hepatocyte-lineage cells," BMC Molecular Biology, 2009, 10:35, pp. 1-11.
Mitaka et al., "Multiple Cell Cycles Occur in Rat Hepatocytes Cultured in the Presence of Nicotinamide and Epidermal Growth Factor," Hepatology, 1991, vol. 13, No. 1, pp. 21-30.
Miyanari et al., "Control of ground-state pluripotency by allelic regulation of Nanog," Nature, 2012, vol. 483, pp. 470-473 (6 pages).
Nakamura et al., "L-Proline is an Essential Amino Acid for Hepatocyte Growth in Culture," Biochemical and Biophysical Research Communications, 1984, vol. 122, No. 3, pp. 884-891.

(Continued)

*Primary Examiner* — Thaian N Ton
*Assistant Examiner* — David A. Montanari
(74) *Attorney, Agent, or Firm* — Kilyk & Bowersox, P.L.L.C.

(57) ABSTRACT

Methods of producing hepatocyte lineage cells are provided. The method can include transfecting a cell with one or more expression vectors. For example, a cell can be transfected with a first expression vector containing a first gene that encodes CCAAT/enhancer binding protein alpha (CEBPA), a second expression vector containing a second gene that encodes CCAAT/enhancer binding protein beta (CEBPB), a third expression vector containing a third gene that encodes forkhead box A1 (FOXA1), and a fourth expression vector containing a fourth gene that encodes forkhead box A3 (FOXA3). The method can include culturing the transfected cell obtained in a growth environment. The transfected cell can be cultured in Williams' E medium, ReproFF (feeder-free media maintaining pluripotency) medium, or both. Transfected and/or hepatocyte lineage cells obtained by a method of the present invention are also provided.

43 Claims, 5 Drawing Sheets

Specification includes a Sequence Listing.

(56) References Cited

PUBLICATIONS

Pretlow, II et al., "Separation of Hepatocytes from Suspensions of Mouse Liver Cells Using Programmed Gradient Sedimentation in Gradients of Ficoll in Tissue Culture Medium," Analytical Biochemistry, 1973, vol. 55, pp. 114-122.

Shibata et al., "Easy stable transfection of a human cancer cell line by electrogene transfer with an Epstein-Barr virus-based plasmid vector," Med Mol Morphol, 2007, vol. 40, pp. 103-107.

Si-Tayeb et al., "Highly Efficient Generation of Human Hepatocyte-Like Cells from Induced Pluripotent Stem Cells," Hepatology, 2010, vol. 51, pp. 297-305.

Simeonov et al., "Direct Reprogramming of Human Fibroblasts to Hepatocyte-Like Cells by Synthetic Modified mRNAs," PLOS ONE, 2014, vol. 9, No. 6, e100134, pp. 1-11.

Song et al., "Efficient generation of hepatocyte-like cells from human induced pluripotent stem cells," Cell Research, 2009, vol. 19, No. 11, pp. 1233-1242.

Takahashi et al., "Induction of Pluripotent Stem Cells from Adult Human Fibroblasts by Defined Factors," Cell, 2007, vol. 131, pp. 861-872.

Takayama et al., "Efficient Generation of Functional Hepatocytes From Human Embryonic Stem Cells and Induced Pluripotent Stem Cells by HNF4alpha Transduction," Molecular Therapy, 2012, vol. 20, No. 1, pp. 127-137.

Takeba et al., "Comparative Study of Culture Conditions for Maintaining CYP3A4 and Atp-Binding Cassette Transporters Activity in Primary Cultured Human Hepatocytes," Journal of Pharmacological Sciences, 2011, vol. 115, pp. 516-524.

Takebe et al., "Vascularized and functional human liver from an iPSC-derived organ bud transplant," Nature, 2013, vol. 499, pp. 481-484 (5 pages).

Tanaka et al., "Construction of Epstein-Barr Virus-Based Expression Vector Containing Mini-OriP," Biochemical and Biophysical Research Commununications, 1999, vol. 264, No. 3, pp. 938-943.

Tomizawa et al., "Hepatocytes Deficient in CCAAT/Enhancer Binding Protein alpha (C/EBPalpha) Exhibit both Hepatocyte and Biliary Epithelial Cell Character," Biochemical and Biophysical Research Communications, 1998, vol. 249, No. 1, pp. 1-5.

Tomizawa et al., "An Optimal Medium Supplementation Regimen for Initiation of Hepatocyte Differentiation in Human Induced Pluripotent Stem Cells," Journal of Cellular Biochemistry, 2015, vol. 116, pp. 1479-1489.

Tomizawa et al., "Dual Gene Expression in Embryoid Bodies Derived from Human Induced Pluripotent Stem Cells Using Episomal Vectors," Tissue Engineering: Part A, 2014, vol. 20, Nos. 23 and 24, pp. 3154-3162.

Tomizawa et al., "Single-step protocol for the differentiation of human-induced pluripotent stem cells into hepatic progenitor-like cells," Biomedical Reports, 2013, vol. 1, pp. 18-22.

Tomizawa et al., "Transcription factors and medium suitable for initiating the differentiation of human induced pluripotent stem cells to the hepatocyte lineage," Journal of Cellular Biochemistry, 2016, DOI 10.1002/jcb.25494, pp. 1-44.

Van Wenum et al., "Bioartificial livers in vitro and in vivo: tailoring biocomponents to the expanding variety of applications," Expert Opin. Biol. Ther., 2014, vol. 14, No. 12, pp. 1745-1760 (18 pages).

Wu et al., "Effect of pyridine on the expression of cytochrome P450 isozymes in primary rat hepatocyte culture," Molecular and Cellular Biochemistry, 1997, vol. 173, pp. 103-111.

Xu et al., "Chromatin "pre-pattern" and epigenetic modulation in the cell fate choice of liver over pancreas in the endoderm," Nucleus, 2012, vol. 3, No. 2, pp. 150-154.

Yamasaki et al., "Suppression of C/EBPalpha expression in periportal hepatoblasts may stimulate biliary cell differentiation through increased Hnf6 and Hnf1b expression," Development, 2006, vol. 133, pp. 4233-4243.

Yates et al., "Stable replication of plasmids derived from Epstein-Barr virus in various mammalian cells," Nature, 1985, vol. 313, pp. 812-815.

Zaret et al., "Pioneer transcription factors: establishing competence for gene expression," Genes & Development, 2011, vol. 25, pp. 2227-2241.

Zaret et al., "Pioneer Factors, Genetic Competence, and Inductive Signaling: Programming Liver and Pancreas Progenitors from the Endoderm," Cold Spring Harbor Symposia on Quantitative Biology, 2008, vol. LXXIII, pp. 119-126.

\* cited by examiner

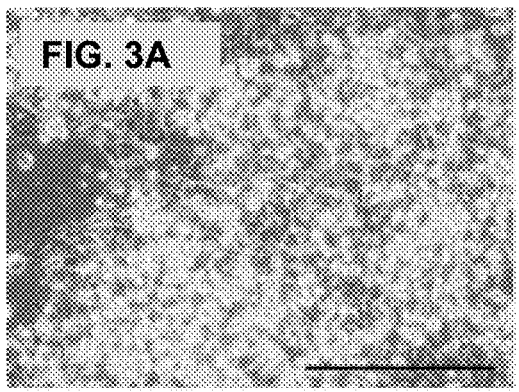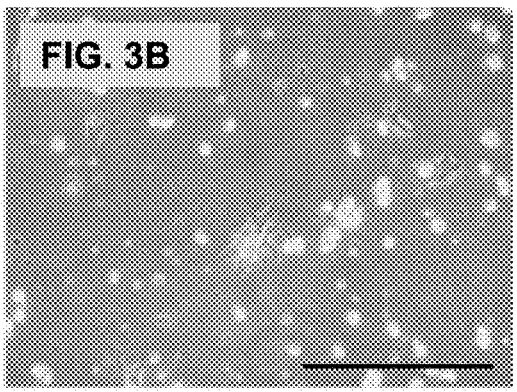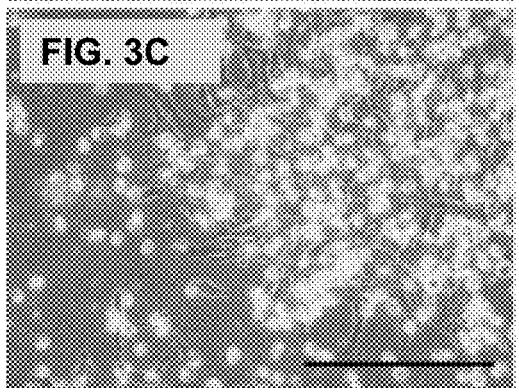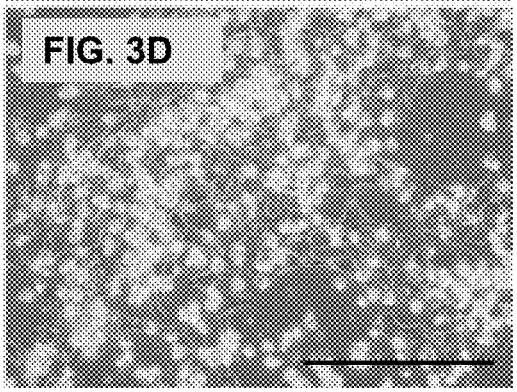

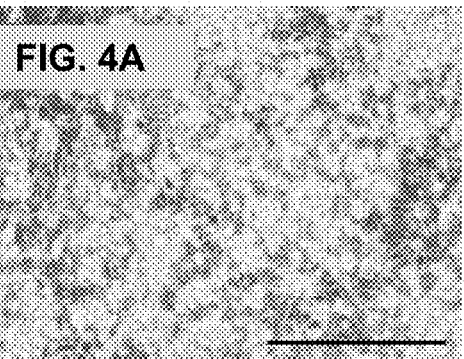
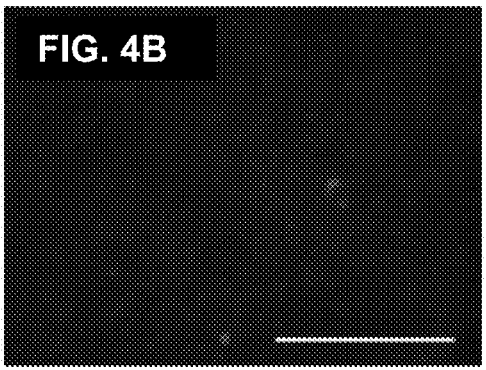
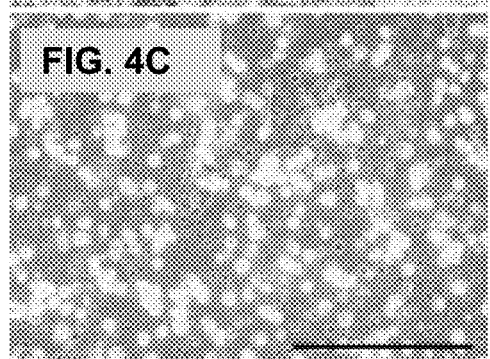
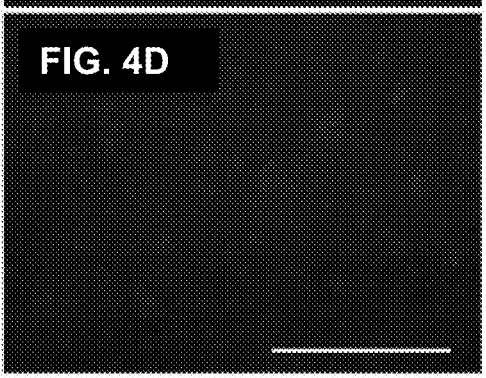
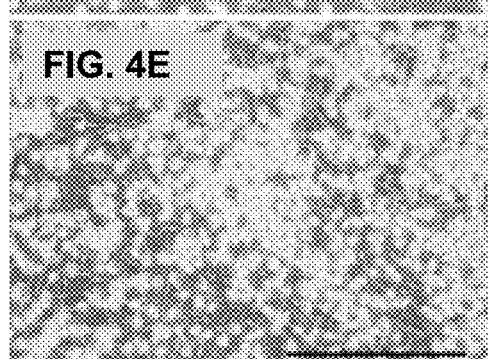

METHODS AND MATERIALS FOR OBTAINING HEPATOCYTE LINEAGE CELLS

This application claims the benefit under 35 U.S.C. § 119(e) of prior U.S. Provisional Patent Application No. 62/288,516, filed Jan. 29, 2016, which is incorporated in its entirety by reference herein.

BACKGROUND OF THE INVENTION

The present invention relates to methods of obtaining hepatocyte lineage cells, intermediate cells, and hepatocytes; the resulting cells; as well as materials for producing the same.

Human induced pluripotent stem (iPS) cells can be generated using four reprogramming factors [Takahashi et al., 2007]. IPS cells have the ability to differentiate into various types of cells and can be applied in regenerative medicine [Hirschi et al., 2014]. Hepatic insufficiency is a fatal condition. If hepatocytes can be produced from iPS cells, they could be used for transplantation in patients with hepatic insufficiency [Chang et al., 2012; van Wenum et al., 2014].

Several protocols on the differentiation of iPS cells to hepatocytes have been reported [DeLaForest et al., 2011; Inamura et al., 2010; Si-Tayeb et al., 2010; Song et al., 2009; Takayama et al., 2012; Zaret et al., 2008]. Most of these apply growth factors sequentially, simulating hepatocyte differentiation in fetal liver [DeLaForest et al., 2011; Si-Tayeb et al., 2010; Song et al., 2009; Takayama et al., 2012]. Another approach is to construct a three-dimensional liver using a combination of iPS cells, human umbilical vascular endothelial cells, and human mesenchymal cells [Takebe et al., 2013]. Only a few protocols have used transcription factors [Inamura et al., 2010; Takayama et al., 2012; Tomizawa et al., 2013].

FOXA1 can open compacted chromatin to initiate transcription, and is called the "pioneering factor" [Xu and Zaret, 2012]. FOXA1 is involved in liver development [Zaret and Carroll, 2011]. FOXA3 binds the promoters of hepatocyte-specific genes, such as AFP and albumin, and upregulates their expression [Costa et al., 2003]. The combination of hepatocyte nuclear factor 1A and FOXA1, FOXA3, or hepatocyte nuclear factor 4A can promote transdifferentiation of human fibroblasts to hepatocyte-like cells [Simeonov and Uppal, 2014]. With another combination of FOXA3, hepatocyte nuclear factor 1A and hepatocyte nuclear factor 4A, human fibroblasts have been transdifferentiated to functional hepatocytes [Hang et al., 2014].

Williams' Medium E (WE) was originally established to isolate hepatocytes from a mixture of fibroblasts for rat primary hepatocyte culture [Pretlow and Williams, 1973]. Drug metabolism is preserved in rat primary hepatocytes cultured in WE [Takeba et al., 2011; Wu et al., 1997]. Gluconeogenesis and urea cycle—hepatocyte-specific functions—are also maintained in WE [Dabos et al., 2004; Farghali et al., 2002]. These findings indicate that WE is suitable for hepatocyte culture without loss of hepatocyte-specific functions.

Transcription factors are involved in liver development [Takebe et al., 2013]. CCAAT/enhancer binding protein alpha (CEBPA) was cloned by Antonson et al [Antonson and Xanthopoulos, 1995]. Hepatocytes deficient in CEBPA have the characteristics of both hepatocytes and bile duct epithelial cells [Tomizawa et al., 1998]. The characteristics of biliary epithelial cells can be enhanced in hepatoblasts with lower expression of CEBPA [Yamasaki et al., 2006]. CEBPA might promote the differentiation of hepatoblasts to mature hepatocytes. CCAAT/enhancer binding protein beta (CEBPB) was cloned by Akira et al [Akira et al., 1990]. CEBPB is involved in the differentiation of hepatocytes [Kheolamai and Dickson, 2009]. A combination of transcription factors is, however, not known to initiate differentiation of iPS cells to hepatocytes.

Accordingly, a need exists for new methods of producing hepatocyte lineage cells.

SUMMARY OF THE PRESENT INVENTION

A feature of the present invention is to provide a method of producing hepatocyte lineage cells.

Another feature of the present invention is to provide methods that employ various cell types as starting points for producing hepatocyte lineage cells.

A further feature of the present invention is to utilize one or more gene containing expression vectors to aid in the differentiation of cells into hepatocyte lineage cells.

An additional feature of the present invention is to utilize one or more growth media to aid in the differentiation of cells into hepatocyte lineage cells.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a method of producing hepatocyte lineage cells. The method can include transfecting a cell with one or more expression vectors. For example, a cell can be transfected with a first expression vector containing a first gene that encodes CCAAT/enhancer binding protein alpha (CEBPA), a second expression vector containing a second gene that encodes CCAAT/enhancer binding protein beta (CEBPB), a third expression vector containing a third gene that encodes forkhead box A1 (FOXA1), and a fourth expression vector containing a fourth gene that encodes forkhead box A3 (FOXA3). The method can include culturing the transfected cell obtained in a growth environment.

The present invention also relates to a transfected and/or hepatocyte lineage cell obtained by a method of the present invention.

The present invention further relates to a method of producing hepatocyte lineage cells including one or more steps. A step (a) can include introducing four expression vectors into induced pluripotent stem (iPS) cells, wherein the expression vectors are an expression vector containing a gene that encodes CCAAT/enhancer binding protein alpha (CEBPA), an expression vector containing a gene that encodes CCAAT/enhancer binding protein beta (CEBPB), an expression vector containing a gene that encodes forkhead box A1 (FOXA1), and an expression vector containing a gene that encodes forkhead box A3 (FOXA3). A step (b) can include culturing the cells obtained in step (a) in a growth environment.

It is to be understood that both the foregoing general description and the following detailed description are exem-

BRIEF DESCRIPTION OF DRAWINGS

FIGS. 3A-3D are magnified images of 201B7 cells transfected with four transcription factors and cultured in four media.

FIGS. 4A-4H are magnified images of 201B7 cells transfected with pEBNK-Hyg/Cherry (CherryPicker1) and cultured in various media and observed with a microscope under white light (FIGS. 4A, 4C, 4E, and 4G) or a fluoroscope (FIGS. 4B, 4D, 4F, or 4H).

DETAILED DESCRIPTION OF THE PRESENT INVENTION

Figure 1A:
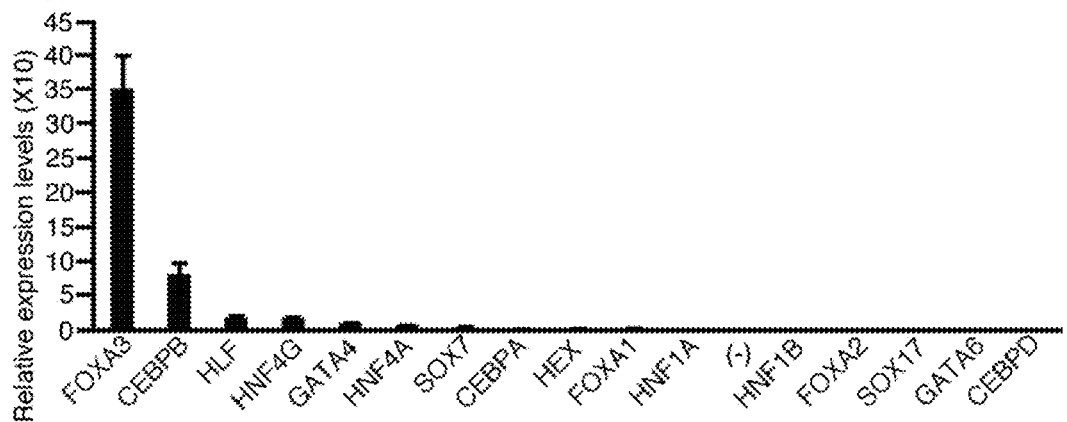
FIGS. 1A and 1B are graphs of relative expression levels based on alpha-feto protein and albumin in 201B7 cells transfected with various transcription factors.

The present invention relates to a method of producing hepatocyte lineage cells. The method can include transfecting a cell with one or more expression vectors. For example, a cell can be transfected with a first expression vector containing a first gene that encodes CCAAT/enhancer binding protein alpha (CEBPA), a second expression vector containing a second gene that encodes CCAAT/enhancer binding protein beta (CEBPB), a third expression vector containing a third gene that encodes forkhead box A1 (FOXA1), and a fourth expression vector containing a fourth gene that encodes forkhead box A3 (FOXA3). The method can include culturing the transfected cell obtained in a growth environment.

The method can further include differentiating the transfected cell into a hepatocyte lineage cell. The culturing can result in the differentiation of the transfected cell into a hepatocyte lineage cell. The two or more of the four genes can act synergistically to differentiate the cell into a hepatocyte lineage cell. The synergism can refer to the time, efficiency, and/or productivity of cell differentiation. Synergism can be super-additive or simply greater than the differentiation caused by a single gene or a smaller subset of genes. The method can further include obtaining a hepatocyte lineage cell from the transfected cell. The hepatocyte lineage cell can be an immortal hepatocyte lineage cell. The hepatocyte lineage cell can express at least one cell surface marker characteristic of hepatocytes. The hepatocyte lineage cell can express alpha-feto protein, albumin, or both. Differentiation can be partial or complete. Differentiation can be further aided by adding one or more additional genes beyond the first four genes, for example, a fifth gene, a sixth gene, and so on.

The transfected cell can be cultured in a medium formulated for hepatocyte differentiation, hepatocyte growth, or both. The transfected cell can be cultured in Williams' E medium in the growth environment. The transfected cell can be cultured in Williams' E medium after culturing in the growth environment. For example, the transfected cell can be cultured in Williams' E Medium (aka, William's E Medium, Williams' Medium E). Other appropriate media can include ReproFF (feeder-free media maintaining pluripotency), Leibovitz-15 (L15), and Dulbecco's Modified Eagle Medium/Nutrient F-12 Ham (DF12). Media can be used individually or in combination. When used in combination, for example, media can be used contemporaneously as a mixture or sequentially. Any appropriate Williams' E Medium can include one or more of sodium bicarbonate, L-glutamine, phenol red, and 4-(2-hydroxyethyl)-1-piperazineethanesulfonic acid (HEPES) buffer as components. Williams' E Medium can exclude one or more of sodium bicarbonate, L-glutamine, phenol red, and 4-(2-hydroxyethyl)-1-piperazineethanesulfonic acid (HEPES) buffer. Williams' E Medium can be supplied as dry powder or as a liquid medium. Williams' E medium can be supplemented with fetal bovine serum (FBS). Williams' E medium can be obtained from any suitable supplier, for example, ThermoFisher Scientific, Sigma-Aldrich, or Lonza. Examples of Williams' E Medium available from ThermoFisher Scientific include 12551-Williams' Medium E (Cat. No. 12551032); A12176—Williams' Medium E, no Phenol Red (Cat. No. A1217601); 32551—Williams' Medium E, GlutaMAX™ (Cat. Nos. 32551020, 32551087); and 22551—Williams' Medium E (Cat. No. 22551022, 22551089). Table 1 sets forth the formulation for 12551—Williams' Medium E and additionally example concentration ranges for components. For any of the specified components listed here, it is to be understood that these amounts can vary from about 1.0% to about 20%, or from about 1% to about 10%, from about 1.0% to about 5.0%, from about 0.5% to about 2.0%, or from about 0.1% to about 0.5% of the value given. Optionally, one or more of the listed components can be omitted or an equivalent component substituted, for example, two components, three components, four components, five components, ten components, 15 components, 25 components, or more components, or any intervening number of components can be omitted or substituted for.

TABLE 1

| Components | Molecular Weight | Conc. (mg/L) | Conc. Range (mg/L) | mM |
|---|---|---|---|---|
| Amino Acids | | | | |
| Glycine | 75.0 | 50.0 | 40.0-60.0 | 0.6666667 |
| L-Alanine | 89.0 | 90.0 | 80.0-100.0 | 1.011236 |
| L-Arginine | 174.0 | 50.0 | 40.0-60.0 | 0.28735632 |
| L-Asparagine-H2O | 150.0 | 20.0 | 15.0-25.0 | 0.13333334 |
| L-Aspartic acid | 133.0 | 30.0 | 20.0-40.0 | 0.22556391 |
| L-Cysteine | 121.0 | 40.0 | 30.0-50.0 | 0.3305785 |
| L-Cystine 2HCl | 313.0 | 26.07 | 20.0-30.0 | 0.08329073 |
| L-Glutamic Acid | 147.0 | 50.0 | 40.0-60.0 | 0.34013605 |
| L-Histidine | 155.0 | 15.0 | 10.0-20.0 | 0.09677419 |

TABLE 1-continued

| Components | Molecular Weight | Conc. (mg/L) | Conc. Range (mg/L) | mM |
|---|---|---|---|---|
| L-Isoleucine | 131.0 | 50.0 | 40.0-60.0 | 0.3816794 |
| L-Leucine | 131.0 | 75.0 | 65.0-85.0 | 0.57251906 |
| L-Lysine hydrochloride | 183.0 | 87.46 | 75.0-95.0 | 0.47792348 |
| L-Methionine | 149.0 | 15.0 | 10.0-20.0 | 0.10067114 |
| L-Phenylalanine | 165.0 | 25.0 | 20.0-30.0 | 0.15151516 |
| L-Proline | 115.0 | 30.0 | 20.0-40.0 | 0.26086956 |
| L-Serine | 105.0 | 10.0 | 5.0-15.0 | 0.0952381 |
| L-Threonine | 119.0 | 40.0 | 30.0-50.0 | 0.33613446 |
| L-Tryptophan | 204.0 | 10.0 | 5.0-15.0 | 0.04901961 |
| L-Tyrosine disodium salt dihydrate | 261.0 | 50.65 | 40.0-60.0 | 0.19406131 |
| L-Valine | 117.0 | 50.0 | 40.0-60.0 | 0.42735043 |
| Vitamins | | | | |
| Ascorbic Acid | 176.0 | 2.0 | 1.5-2.5 | 0.011363637 |
| Biotin | 244.0 | 0.5 | 0.25-0.75 | 0.00204918 |
| Choline chloride | 140.0 | 1.5 | 1.0-2.0 | 0.010714286 |
| D-Calcium pantothenate | 477.0 | 1.0 | 0.5-1.5 | 0.002096436 |
| Ergocalciferol | 397.0 | 0.1 | 0.05-0.15 | 2.52E−04 |
| Folic Acid | 441.0 | 1.0 | 0.5-1.5 | 0.002267574 |
| Menadione sodium bisulfate | 276.0 | 0.01 | 0.005-0.015 | 3.62E−05 |
| Niacinamide | 122.0 | 1.0 | 0.5-1.5 | 0.008196721 |
| Pyridoxal hydrochloride | 204.0 | 1.0 | 0.5-1.5 | 0.004901961 |
| Riboflavin | 376.0 | 0.1 | 0.05-0.15 | 2.66E−04 |
| Thiamine hydrochloride | 337.0 | 1.0 | 0.5-1.5 | 0.002967359 |
| Vitamin A (acetate) | 328.0 | 0.1 | 0.05-0.15 | 3.05E−04 |
| Vitamin B12 | 1355.0 | 0.2 | 0.1-0.3 | 1.48E−04 |
| alpha Tocopherol phos. Na salt | 554.7 | 0.01 | 0.005-0.015 | 1.80E−05 |
| i-Inositol | 180.0 | 2.0 | 1.0-3.0 | 0.011111111 |
| Inorganic Salts | | | | |
| Calcium Chloride (CaCl2) (anhyd.) | 111.0 | 200.0 | 150.0-250.0 | 1.8018018 |
| Cupric sulfate (CuSO4—5H2O) | 250.0 | 1.00E−04 | 1.00E−05-1.00E−03 | 4.00E−07 |
| Ferric nitrate (Fe(NO3)—9H2O) | 404.0 | 1.00E−04 | 1.00E−05-1.00E−03 | 2.48E−07 |
| Magnesium Sulfate (MgSO4) (anhyd.) | 120.0 | 97.67 | 85.0-100.0 | 0.8139166 |
| Manganese chloride (MnCl2—4H2O) | 198.0 | 1.00E−04 | 1.00E−05-1.00E−03 | 5.05E−07 |
| Potassium Chloride (KCl) | 75.0 | 400.0 | 350.0-450.0 | 5.3333335 |
| Sodium Bicarbonate (NaHCO3) | 84.0 | 2200.0 | 2000.0-2500.0 | 26.190475 |
| Sodium Chloride (NaCl) | 58.0 | 6800.0 | 6000.0-7500.0 | 117.24138 |
| Sodium Phosphate monobasic (NaH2PO4) anhydrous | 138.0 | 140.0 | 120.0-160.0 | 1.0144928 |
| Zinc sulfate (ZnSO4—7H2O) | 288.0 | 2.00E−04 | 2.00E−05-2.00E−03 | 6.94E−07 |
| Other Components | | | | |
| D-Glucose (Dextrose) | 180.0 | 2000.0 | 1750-2500 | 11.111111 |
| Glutathione (reduced) | 307.0 | 0.05 | 0.04-0.06 | 1.63E−04 |
| Methyl linoleate | 295.0 | 0.03 | 0.02-0.04 | 1.02E−04 |
| Phenol Red | 376.4 | 10.0 | 0.5-15.0 | 0.026567481 |
| Sodium Pyruvate | 110.0 | 25.0 | 20.0-30.0 | 0.22727273 |

The transfected cell can be cultured for any appropriate length of time. For example, the transfected cell can be cultured for at least five minutes, at least fifteen minutes, at least thirty minutes, at least forty-five minutes, at least one hour, at least two hours, at least three hours, at least five hours, at least 12 hours, at least one day, at least three days, at least seven days (one week), at least eight days, at least ten days, at least twelve days, at least 15 days, at least 20 days, at least 28 days, at least one month, at least six weeks, at least two months, at least three months, at least six months, at least nine months, at least one year, less than five minutes, more than a year, or any intervening period. The transfected cell can be cultured, for example, for from about 4 days to about 12 days. The transfected cell can be cultured, for example, for at least 7 days or greater than seven days. The duration of culturing can refer to the total duration of culturing the transfected cell, or to a segment or period thereof. For example, the duration can refer to culturing the cell in a growth environment, or in a particular growth or cell culture medium, or a series of sequential growth or cell culture media, a period before differentiation is complete, or a period subsequent to differentiation. The transfected cell can be cultured until at least one marker characteristic of a hepatocyte lineage cell is expressed above a recognized threshold. The marker can be associated with an immature hepatocyte, a mature hepatocyte, or both. The transfected cell can be cultured until expression of a marker of the original cell falls below a recognized threshold. The transfected cell can be cultured until it possesses the morphology of a hepatocyte lineage cell and/or a hepatocyte.

Any suitable cell can be transfected. The cell can be a vertebrate cell. The cell can be a mammalian cell, for example, a rodent cell, a murine cell, a primate cell, or a human cell. The cell can be a stem cell. For example, the cell can be a pluripotent stem cell, an induced pluripotent stem (iPS) cell, a 201B7 iPS cell, or an embryonic stem cell. The cell can be a somatic cell or adult cell. For example, the cell can be a fibroblast.

Transfection of the cell can be carried out using any appropriate technique suitable for introducing the expression vectors into the cell. Any suitable number of expression vectors can be used, for example, at least four expression vectors can be used, for example, at least four different expression vectors can be used. Any suitable expression vector or combination of expression vectors can be used. A mammalian vector or a mammalian plasmid can be used. An artificial vector can be used. A plasmid can be used. An episomal plasmid or episomal vector can be used. An adenoviral vector, an adeno-associated viral (AAV) vector, or any combination thereof can be used. The first, second, third, and fourth genes can be distributed among one, two, three, or four expression vectors. For example, all four genes can be on the same expression vector or each gene can be contained in its own expression vector. A single copy or multiple copies of a particular expression vector and/or gene can be transfected into a cell. One or more copies of a particular gene can be present in any given expression vector.

The cell can be transfected with two or more of the expression vectors, for example, all four expression vectors, simultaneously. The cell can be transfected with one or more of the expression vectors sequentially. There can be a delay between the transfection of any two expression vectors. For example, there can be a delay of less than 1 minute, at least 1 minute, at least two minutes, at least five minutes, at least 10 minutes, at least 15 minutes, at least 30 minutes, at least one hour, at least three hours, at least six hours, at least 12 hours, at least one day, at least two days, at least three days, at least one week, or any intervening length of time between introduction of two or more of the expression vectors. One or more tests can be performed to verify successful introduction of one or more of the expression vectors into the cell. The transfection of one or more of the expression vectors can be transient with respect to at least one transcription factor or gene. The transfection of one or more of the expression vector can be stable with respect to at least one expression vector or gene. One or more of the genes can be incorporated into the genomic DNA of the cell.

Any step, combination of steps, or the entire method can be performed, in vivo, in vitro, or both. For example, the transfection can be performed in vitro, the culturing can be performed in vitro, or both. The growth environment can be an in vitro growth environment, an in vivo growth environment, or both. The growth environment can include a liquid medium, a solid support, or both. For example, a liquid growth environment can be used initially and then a solid growth environment. A growth environment can be conducive to formation of liver tissue, a portion of a liver, or a complete liver. Differentiated cells can be transplanted into a mammalian recipient, for example, a rodent such as a mouse or a primate such as a human.

The expression of one or more of the genes can be controlled. The expression of one or more of the genes can be fixed or automatic. At least one or all of the genes can be constitutively activated. At least one or all of the genes can be inducible. For example, at least one inducible gene can be inducible by growth in a suitable medium, for example, Williams' E medium. A gene can be induced, for example, by the gene product of one of the other genes or a gene product induced by one of the other genes, directly or indirectly. Control of a gene can be regulated, for example, through one or more elements on the expression vector containing the gene. Such elements can include, for example, a promoter, an enhancer, a ribosmal binding site, an inducer, a suppressor, a selectable marker, or the like.

The present invention also relates to a transfected and/or hepatocyte lineage cell obtained by a method of the present invention. The cell can be immortal or have a limited number of replication cycles. The cells can be in the form of cells in a cell culture in a liquid, solid, or liquid/solid support. The cells can be in the form of a tissue or organ, for example, a liver, suitable for implantation into an organism.

The present invention further relates to a method of producing hepatocyte lineage cells including one or more steps. A step (a) can include introducing four expression vectors into induced pluripotent stem (iPS) cells, wherein the expression vectors are an expression vector containing a gene that encodes CCAAT/enhancer binding protein alpha (CEBPA), an expression vector containing a gene that encodes CCAAT/enhancer binding protein beta (CEBPB), an expression vector containing a gene that encodes forkhead box A1 (FOXA1), and an expression vector containing a gene that encodes forkhead box A3 (FOXA3). A step (b) can include culturing the cells obtained in step (a) in a growth environment. The cells obtained in step (a) can be cultured in any suitable medium, for example, Williams' E medium. The cells obtained in step (a) and (b) can be cultured in any suitable medium, for example, Williams' E medium. The cells obtained in step (a) can be cultured for any suitable period of time, for example, at least seven days.

The present invention will be further clarified by the following examples, which are intended to be exemplary of the present invention.

EXAMPLES

Transcription factors and culture media were investigated to determine the conditions to initiate the differentiation of human induced pluripotent stem (iPS) cells most efficiently. These investigations are relevant to obtaining hepatocyte lineage cells from any suitable cell, for example, stem cells or somatic cells.

The expression of genes in human adult liver was compared with that in 201B7 cells (iPS cells) using cDNA microarray analysis. Episomal plasmids expressing transcription factors were constructed. 201B7 cells were transfected with the episomal plasmids and cultured in ReproFF (feeder-free media maintaining pluripotency), Leibovitz-15 (L15), Williams' E (WE), or Dulbecco's Modified Eagle Medium/Nutrient F-12 Ham (DF12) for seven days. 12551-Williams' Medium E (ThermoFisher Scientific) was used as the WE (see Table 1) in the examples. RNA was isolated and subjected to real-time quantitative PCR to analyze the expression of alpha-feto protein (AFP) and albumin. cDNA microarray analysis revealed 16 transcription factors that were upregulated in human adult liver relative to that in 201B7 cells. Episomal plasmids expressing these 16 genes were transfected into 201B7 cells.

CCAAT/enhancer binding protein alpha (CEBPA), CCAAT/enhancer binding protein beta (CEBPB), forkhead box A1 (FOXA1), and forkhead box A3 (FOXA3) up-regulated AFP and down-regulated Nanog. These four genes were further analyzed. The expression of AFP and albumin was the highest in 201B7 cells transfected with the combination of CEBPA, CEBPB, FOXA1, and FOXA3 and cultured in WE. The combination of CEBPA, CEBPB, FOXA1, and FOXA3 was suitable for 201B7 cells to initiate differentiation to the hepatocyte lineage and WE was the most suitable medium for culture after transfection.

FOXA1 and FOXA3 enhanced the expression of AFP and albumin in 201B7 cells. These results indicate that FOXA1 and FOXA3 initiated hepatocyte differentiation synergistically with CEBPA and CEBPB. These findings clearly show that FOXA1 and FOXA3 are involved in hepatocyte differentiation. The results also indicate that the combination of CEBPA, CEBPB, FOXA1, and FOXA3 promoted iPS cell differentiation to the hepatocyte lineage. The highest levels of AFP and albumin were obtained in 201B7 cells transfected with the combination of CEBPA, CEBPB, FOXA1, and FOXA3 and cultured in WE. These results further indicate that WE is suitable for initiating the differentiation of iPS cells to the hepatocyte lineage after transfection with the combination of CEBPA, CEBPB, FOXA1, and FOXA3.

Accordingly, the combination of CEBPA, CEBPB, FOXA1, and FOXA3 was suitable for initiating the differentiation of 201B7 cells to the hepatocyte lineage. WE was the most suitable medium for culture after transfection. The details of these experiments are described in the following numbered examples.

Example 1 cDNA microarray analysis revealed transcription factors that were upregulated in human adult liver relative to that in 201B7 cells. These genes were further investigated to identify the transcription factors involved in hepatocyte differentiation or hepatocyte-specific functions. 16 genes were selected for further analyses (Table 2). Original plasmids harboring the cDNA of the 16 genes were obtained as gifts or purchased and used for subcloning into episomal vectors. Finally, episomal vectors harboring the 16 genes were constructed.

protein 6, HEX: hematopoietically expressed homeobox, HLF: hepatic leukemia factor, HNF1A: hepatocyte nuclear factor 1 alpha, HNF1B: hepatocyte nuclear factor 4 beta, HNF4G: hepatocyte nuclear factor 4 gamma, SOX7: sex determining region Y box 7, SOX17: sex determining region Y box 17, PCR: fragment amplified with PCR, cloned into cloning vectors, and sequence confirmed, (–): directly subcloned from the original plasmids to episomal plasmid.

201B7 cells were purchased from RIKEN Cell Bank (Tsukuba, Japan) and cultured in ReproFF (Reprocell) (Yokohama, Japan) in 6-well plates (Asahi Techno Glass) (Funabashi, Japan) coated with Matrigel™ (Becton Dickinson) (Franklin Lakes, N.J., USA) under feeder-free conditions. The cells were incubated in 5% carbon dioxide at 37° C. in a humidified incubator. The cells were then harvested with Accutase® (Innovative Cell Technologies, Inc.) (San Diego, Calif., USA) and spread onto new 6-well plates and observed under a microscope (CKX41N-31PHP) (Olympus) (Tokyo, Japan).

cDNA microarray analysis was performed by Bio Matrix Research, Inc. (Nagareyama, Japan). The expression of genes in human adult liver was compared with that in 201B7 cells. Total RNA from human adult liver was purchased from Clontech (Mountain View, Calif., USA). Total RNA from 201B7 cells cultured in ReproFF was isolated and

TABLE 2

| | GenBank | Original plasmid | Restriction site to cloning plasmid | Cloning plasmid | Restriction site to Expression plasmid | Episomal plasmid |
|---|---|---|---|---|---|---|
| CEBPA | U34070 | pG28B5.0 Ref Antonson | (–) | (–) | NruI-EcoR5 into EcoR5 | pEBMulti-Neo pEMMulti-Hyg |
| CEBPB | X52560 | Ref Akira | (–) | (–) | Not1-Kpn1 | pEBNK-Neo pEBNK-Hyg |
| CEBPD | BC105109 | RIKEN IRCB003O22 | EcoR1 | pBluescript SK(–) | EcoR5-BamH1 | pEBMulti-Neo |
| FOXA1 | BC033890 | RIKEN IRAK047019 | EcoR1-BamH1 | pBluescript SK(–) | Xho1-BamH1 | pEBMulti-Neo |
| FOXA2 | NM_021784 | OriGene sc321626 | EcoR1-Pst1 | pBluescript SK(–) | Sal1-BamH1 | pEBMulti-Neo |
| FOXA3 | BC016024 | RIKEN IRAK015C16 | EcoR1-Not1 | pBluescript SK(–) | Xho1-Not1 | pEBMulti-Neo pEBMulti-Hyg |
| GATA4 | NM_002052 | OriGene Sc124037 | Nru1-EcoR1 | pBluescript SK(–) | Kpn1-Not1 | pEBMulti-Neo pEBMunti-Hyg |
| GATA6 | NM_005257 | RIKEN Are07G01 | (–) | (–) | Xho1-BamH1 | pEBMulti-Neo |
| HEX | BC015110 | RIKEN IRAL031O05 | (–) | (–) | Kpn1 | pEBMulti pEBMulti-Hyg |
| HLF | BC036093 | RIKEN IRAK048J15 | Not1-Kpn1 (PCR) | pBluescript SK(–) | Not1-Kpn1 | pEBNK-Neo pEBNK-Neo |
| HNF1A | BC104908 | ATCC 11047178 | EcoR1 | pBluescript SK(–) | Not1-Kpn1 | pEBNK-Neo pEBNK-Hyg |
| HNF1B | BC017714 | RIKEN IRAK0127102 | Not1-Kpn1 (PCR) | pBluescript SK(–) | Not1-Kpn1 | pEBNK-Neo |
| HNF4A | NM_000457 | OriGene Sc123863 | Not1-Kpn1 (PCR) | pBluescript SK(–) | Not1-Kpn1 | pEBNK-Neo pEBNK-Hyg |
| HNF4G | BC105011 | DBNAFORM 8144014 | EcoR1 | pBluescript SK(–) | Sal1-BamH1 | pEBMulti-Neo pEBMulti-Hyg |
| SOX7 | BC071947 | RIKEN IRAL058N22 | Xba1-Kpn1 | pBluescript SK(–) | Not1-Kpn1 | pEBNK-Neo pEBNK-Hyg |
| SOX17 | NM_022454 | RIKEN W01A073N10 | Not1-Kpn1 (PCR) | pBluescript SK(–) | Not1-Kpn1 | pEBNK-Neo pEBNK-Hyg |

Abbreviations/Acronyms in Table 2 are as follows. CEBPA: CCAAT/enhancer binding protein alpha, CEBPB: CCAAT/enhancer binding protein beta, CEBPD: CCAAT/enhancer binding protein delta, FOXA1: forkhead box A1, FOXA2: forkhead box A2, FOXA3: forkhead box A3, GATA4: GATA binding protein 4, GATA6: GATA binding purified with an RNeasy Mini column (Qiagen) (Velno, Netherland). The RNA (10 μg) was labeled using a SuperScript Indirect cDNA Labeling Kit (Invitrogen) and Cy™3 or Cy™5 Mono-Reactive Dye (GE Healthcare, Little Chalfont, UK). The dye-coupled cDNAs were purified using a MiniElute PCR purification kit (Qiagen) and hybridized to an Agilent 44K human 60-mer oligo microarray (Agilent Technologies) (Santa Clara, Calif.) according to the manufacturer's instructions. An Agilent microarray scanner (Agilent Technologies) was used to wash, dry, and scan the slides. A Genespring GX software package (Agilent Technologies) was used to process and analyze the data.

Plasmid construction is briefly presented in Table 2. Original plasmids were kindly provided by Dr. M. Matsumoto (Osaka University, Suita, Japan) and Dr. KG. Xanthopoulos (Karolinska Institute, Stockholm, Sweden) or were purchased from RIKEN DNA Bank (Tsukuba, Japan), OriGene (Rockville, Md., USA), or DNAFORM (Yokohama, Japan). Fragments containing cDNA were subcloned into pBluescriptII SK(−) (Agilent Technologies) by restriction digestion from their original plasmids or were amplified by polymerase chain reaction (PCR). For fragments amplified by PCR, the sequences were confirmed by Bio Matrix Research, Inc. The fragments in pBluescriptII SK(−) were subcloned into pEBMulti-Neo (Wako Pure Chemicals, Osaka, Japan), pEBMulti-Hyg (Wako Pure Chemicals), pEBNK-Neo [Tomizawa et al., 2014], or pEBNK-Hyg [Tomizawa et al., 2014]. pEBMulti-Neo, pEBMulti-Hyg, pEBNK-Neo, and pEBNK-Hyg were episomal plasmids.

Episomal plasmids contain an origin of replication and the nuclear antigen of Epstein-Barr virus. These two factors enable replication of episomal plasmids and distribution to daughter cells after cell division [Yates et al., 1985]. Genes in the plasmids were expressed for at least seven days [Shibata et al., 2007; Tanaka et al., 1999]. The transfected genes were expressed longer from episomal plasmids than from conventional expression plasmids. CCAAT/enhancer binding protein alpha (CEBPA), CCAAT/enhancer binding protein beta (CEBPB), GATA binding protein 6, and hematopoietically expressed homeobox were directly subcloned from their original plasmids to episomal vectors.

PCR for cloning was performed as follows. cDNAs of hepatocyte leukemia factor, hepatocyte nuclear factor 1B, and sex determining region Y box 17 were amplified with LA PCR™ Kit Ver.2.1 (Takara) (Ohtsu, Japan) according to the manufacturer's instructions. Next, 40 cycles of PCR were carried out in the GeneAmp PCR System 9700 (Life Technologies) at 98° C. for 20 s for denaturation and at 68° C. for 3 min for annealing-extension. The templates are presented in Table 2, and their primer sequences are listed in Table 3.

TABLE 3

| Gene name | GenBank | Sequence | Product size (bp) | Annealing-extension temperature (° C.) | Cycles |
|---|---|---|---|---|---|
| HLF, forward | BC036093 | 5'-ATCGTCTAGAATGGA GAAAATGTCCCGACC-3' (SEQ ID NO: 1) | 888 | 68 | 40 |
| HLF, reverse | | 5'-ATCGGGTACCCTACAG GGGCCCGTGCCTGG-3' (SEQ ID NO: 2) | | | |
| HNF1B, forward | BC017714 | 5'-ATCGTCTAGAATGGTGT CCAAGCTCACGTC-3' (SEQ ID NO: 3) | | 68 | 40 |
| HNF1B, reverse | | 5'-ATCGGGTACCTCACCAG GCTTGTAGAGGAC-3' (SEQ ID NO: 4) | 1673 | | |
| SOX17, forward | NM_022454 | 5'-ATCGTCTAGAATGAGCA GCCCGGATGCGGG-3' (SEQ ID NO: 5) | 1245 | 68 | 40 |
| SOX17, reverse | | 5'-ATCGGGTACCTCACACG TCAGGATAGTTGC-3' (SEQ ID NO: 6) | | | |

Abbreviations/Acronyms in Table 3 are as follows. HLF: hepatic leukemia factor, HNF1B: hepatocyte nuclear factor 4 beta, SOX17: sex determining region Y box 17.

Five micrograms of total RNA isolated using Isogen (Nippon Gene) (Tokyo, Japan) was subjected to first-strand cDNA synthesis using superscriptIII reverse transcriptase (Life Technologies) and oligo dT according to the manufacturer's instructions. Fast CYBR Green Master Mix (Life Technologies) was used for real-time qPCR. Real-time quantitative PCR (qPCR) was conducted in the Mini Opticon System (Bio-Rad) (Hercules, Calif., USA). The results were analyzed and displayed by the Mini Opticon System automatically. Primer sequences (pairs) are listed in Table 4.

TABLE 4

| Gene name | GenBank | Sequence | Product size (bp) | Annealing-extension temperature (° C.) | Cycles |
|---|---|---|---|---|---|
| CEBPA, forward | U34070 | 5'-CGGACTTGGTGC GTCTAAGATG-3' (SEQ ID NO: 7) | 148 | 60 | 40 |
| CEBPA, reverse | | 5'-GCATTGGAGCG GTGAGTTTG-3' (SEQ ID NO: 8) | | | |
| CEBPB, forward | X52560 | 5'-AAGCACAGCGA CGAGTACAA-3' (SEQ ID NO: 9) | 155 | 60 | 40 |
| CEBPB, reverse | | 5'-AGCTGCTCCAC CTTCTTCTG-3' (SEQ ID NO: 10) | | | |
| CEBPD, forward | BC105109 | 5'-AGAAGTTGGT GGAGCTGTCG-3' (SEQ ID NO: 11) | 101 | 60 | 40 |
| CEBPD, reverse | | 5'-CAGCTGCTTGA AGAACTGCC-3' (SEQ ID NO: 12) | | | |
| FOXA1, forward | BC033890 | 5'-GGACTTCAAGG CATACGAACAGG-3' (SEQ ID NO: 13) | 163 | 60 | 40 |
| FOXA1, reverse | | 5'-TAGGACGGGTCTG GAATACACACC-3' (SEQ ID NO: 14) | | | |
| FOXA2, forward | NM_021784 | 5'-GATACCTCCTACT ACCAGGG-3' (SEQ ID NO: 15) | 121 | 60 | 40 |
| FOXA2, reverse | | 5'-CACTTGCTCTCT CACTTGTC-3' (SEQ ID NO: 16) | | | |
| FOXA3, forward | BC016024 | 5'-AAGGAGATGCC GAAGGGGTATC-3' (SEQ ID NO: 17) | 129 | 60 | 40 |
| FOXA3, reverse | | 5'-CTGGTAGATTTC ACTCAAGGTCAGC-3' (SEQ ID NO: 18) | | | |
| GATA4, forward | NM_002052 | 5'-TCTCAGTCAGTG CGATGTCTGG-3' (SEQ ID NO: 19) | 197 | 60 | 40 |
| GATA4, reverse | | 5'-AGGAGGGAAGA GGGAAGATTACG-3' (SEQ ID NO: 20) | | | |
| GATA6, forward | NM_005257 | 5'-CCACTCGTGTCTG CTTTTGTGC-3' (SEQ ID NO: 21) | 136 | 60 | 40 |
| GATA6, reverse | | 5'-CCCTTCCCTTC-CAT CTTCTCTCAC-3' (SEQ ID NO: 22) | | | |
| HEX, forward | BC015110 | 5'-GCCCAGTGAACAG AATAAAGGTGC-3' (SEQ ID NO: 23) | 167 | 60 | 40 |
| HEX, reverse | | 5'-CCAATGCCAGTGG TCATCATCC-3' (SEQ ID NO: 24) | | | |

TABLE 4-continued

| Gene name | GenBank | Sequence | Product size (bp) | Annealing-extension temperature (° C.) | Cycles |
|---|---|---|---|---|---|
| HLF, forward | BC036093 | 5'-TCGTCAATCCATC AGCAATGC-3' (SEQ ID NO: 25) | 130 | 60 | 40 |
| HLF, reverse | | 5'-TCCAATACACCC CCATCTCTTG-3' (SEQ ID NO: 26) | | | |
| HNF1A, forward | BC104908 | 5'-ACCTGTCCCAAC ACCTCAAC-3' (SEQ ID NO: 27) | 152 | 60 | 40 |
| HNF1A, reverse | | 5'-CTCATCACCTG TGGGCTCTT-3' (SEQ ID NO: 28) | | | |
| HNF1B, forward | BC017714 | 5'-AAAGAACCCCAG CAAGGAAGAG-3' (SEQ ID NO: 29) | 127 | 60 | 40 |
| NHF1B, reverse | | 5'-ACGGACCTCAG TGACCAAGTTG-3' (SEQ ID NO: 30) | | | |
| NHF4A, forward | NM_000457 | 5'-ACCTCATCCTCC TTCTTCAGGGAC-3' (SEQ ID NO: 31) | 124 | 60 | 40 |
| HNF4A, reverse | | 5'-GCTTTTC-CTCTCCA CTCCAAGTTC-3' (SEQ ID NO: 32) | | | |
| HNF4G, forward | BC105011 | 5'-TCAGTCATTTC ACACCAGC-3' (SEQ ID NO: 33) | 126 | 60 | 40 |
| HNF4G, reverse | | 5'-TGCCAAAAGTG CTATCCTG-3' (SEQ ID NO: 34) | | | |
| SOX7, forward | BC071947 | 5'-ACTCCACTCC AACCTCCAAG-3' (SEQ ID NO: 35) | 151 | 60 | 40 |
| SOX7, reverse | | 5'-GTGGCCAGG AGTGTTCAAAT-3' (SEQ ID NO: 36) | | | |
| SOX17, forward | NM_022454 | 5'-CGCTTTCATGGTG TGGGCTAAGGACG-3' (SEQ ID NO: 37) | 186 | 60 | 40 |
| SOX17, reverse | | 5'-TAGTTGGGGTGGT CCTGCATGTGCTG-3' (SEQ ID NO: 38) | | | |
| RPL19, forward | BC095445 | 5'-CGAATGCCAGA GAAGGTCAC-3' (SEQ ID NO: 39) | 157 | 60 | 40 |
| RPL19, reverse | | 5'-CCATGAGAATC CGCTTGTTT-3' (SEQ ID NO: 40) | | | |
| AFP, forward | NM_001134 | 5'-ACACAAAAAG CCCACTCCAG-3' (SEQ ID NO: 41) | 147 | 60 | 40 |
| AFP, reverse | | 5'-GGTGCATACAGG AAGGGATG-3' (SEQ ID NO: 42) | | | |

TABLE 4-continued

| Gene name | GenBank | Sequence | Product size (bp) | Annealing-extension temperature (° C.) | Cycles |
|---|---|---|---|---|---|
| Albumin, forward | NM_000477 | 5'-GCTCGTGAAACA CAAGCCCAAG-3' (SEQ ID NO: 43) | 114 | 60 | 40 |
| Albumin, reverse | | 5'-GCAAAGCAGGTC TCCTTATCGTC-3' (SEQ ID NO: 44) | | | |
| Nanog. Forward | NM_024865 | 5'-CCGTTTTTGGCTC TGTTTTG-3' (SEQ ID NO: 45) | 187 | 60 | 40 |
| Nanog, reverse | | 5'-TCATCGAAACA CTCGGTGAA-3' (SEQ ID NO: 46) | | | |

Abbreviations/Acronyms in Table 4 are as follows. CEBPA: CCAAT/enhancer binding protein alpha, CEBPB: CCAAT/enhancer binding protein beta, CEBPD: CCAAT/enhancer binding protein delta, FOXA1: forkhead box A1, FOXA2: forkhead box A2, FOXA3: forkhead box A3, GATA4: GATA binding protein 4, GATA6: GATA binding protein 6, HEX: hematopoietically expressed homeobox, HLF: hepatic leukemia factor, HNF1A: hepatocyte nuclear factor 1 alpha, HNF1B: hepatocyte nuclear factor 4 beta, HNF4G: hepatocyte nuclear factor 4 gamma, SOX7: sex determining region Y box 7, SOX17: sex determining region Y box 17, RPL19: ribosomal protein L (RPL) 19, AFP: alpha-feto protein.

To identify candidates promoting hepatocyte differentiation from iPS cells, 210B7 cells were transfected with each episomal vector and cultured in ReproFF for seven days. For transfection, 201B7 cells were plated on 6-well plates or 8-well chamber slides (Matsunami) (Kishiwada, Japan) coated with Matrigel™. The constructed episomal vectors were transfected with FuGENE HD (Clontech) (Mountain View, Calif., USA) according to the manufacturer's instructions. Subsequently, 0.5 µg or 0.16 µg of each episomal plasmid was transfected to each well of the 6- or 8-well chamber slides, respectively. After transfection, the cells were cultured in ReproFF, Leibovitz-15 (L15), Williams' E (WE), or Dulbecco's Modified Eagle Medium/Nutrient F-12 Ham (DF12). L15, WE, and DF12 were supplemented with nicotinamide (1.2 mg/ml) (Wako Pure Chemicals), proline (30 ng/ml) (Wako Pure Chemicals), and 10% knockout serum replacement (Life Technologies). Nicotinamide and proline were added for proliferation of hepatocytes [Mitaka et al., 1991; Nakamura et al., 1984]. For some experiments, the cells were also transfected with pEBNK-Hyg/Cherry [Tomizawa et al., 2014].

Figure 1B:
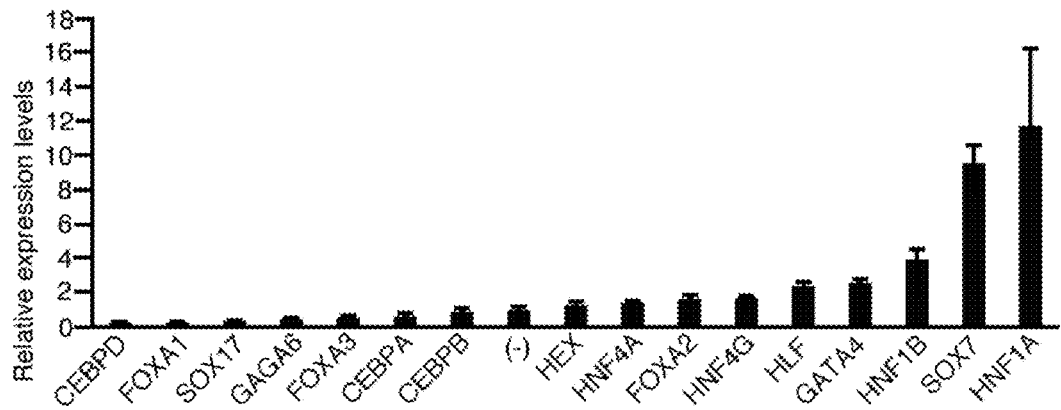

After culture, RNA was isolated and subjected to qPCR to determine AFP (FIG. 1A) and Nanog (FIG. 1B) levels. FIGS. 1A and 1B are graphs showing expression of levels of alpha-feto protein and albumin in 201B7 cells transfected with transcription factors. 201B7 cells were transfected with transcription factors and cultured in ReproFF (Reprocell). After seven days of culture, RNA was isolated and subjected to real-time quantitative PCR to analyze the levels of alpha-feto protein (FIG. 1A) and albumin (FIG. 1B). (–): no transfection. AFP expression was higher in 201B7 cells transfected with 11 of 16 genes than in untransfected cells. Nanog expression was lower in 210B7 cells transfected with seven genes than in untransfected cells. AFP is a marker of immature hepatocytes [Duan et al., 2010]. Nanog is associated with pluripotency [Miyanari and Torres-Padilla, 2012]. Therefore, transcription factors inducing high AFP expression while suppressing Nanog expression would be suitable for initiating hepatocyte differentiation of iPS cells. CEBPA, CEBPB, forkhead box 1A (FOXA1), and forkhead A3 (FOXA3) met these criteria. These four transcription factors were considered candidate genes for hepatocyte differentiation.

Example 2

Figure 2A:
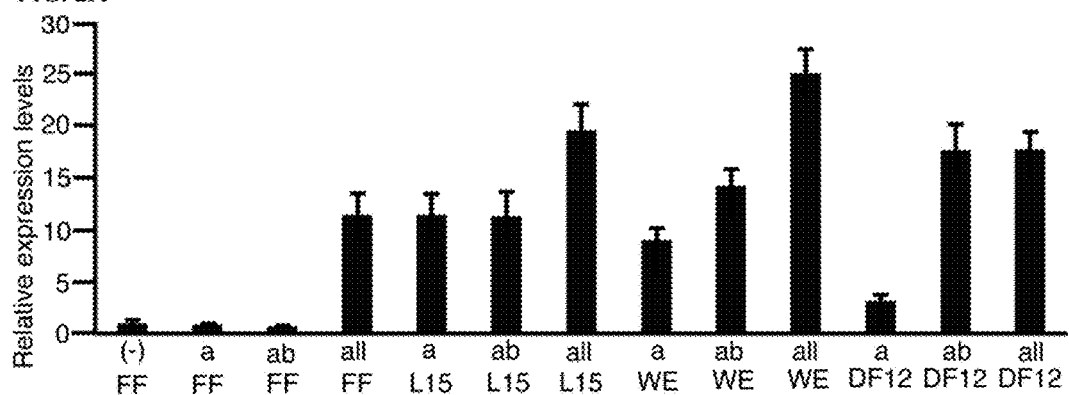
FIGS. 2A and 2B are graphs of relative expression levels of cells transfected with transcription factors and cultured in one of four media.
Figure 2B:
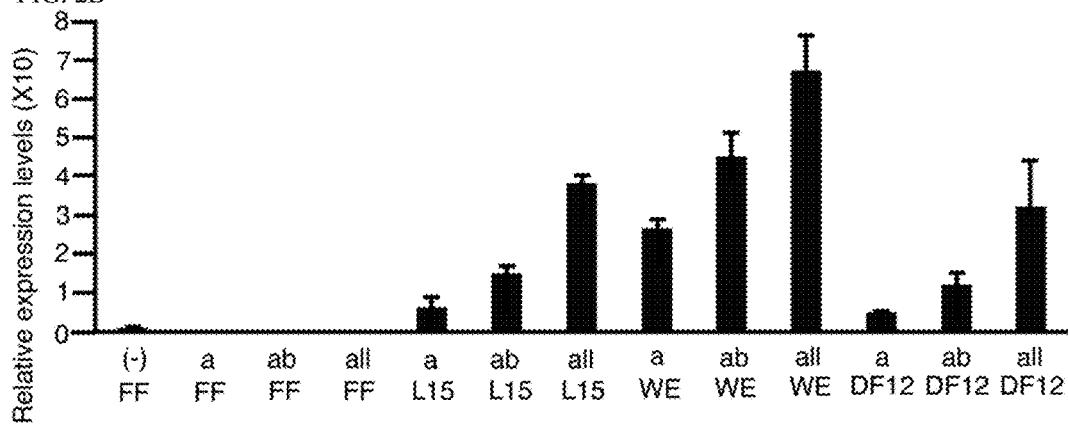

This example examines which combination of transcription factors and which medium would be suitable for differentiation of iPS cells to the hepatocyte lineage. 201B7 cells were transfected with CEBPA, CEBPA, and CEBPB and a combination of CEBPA, CEBPB, FOXA1, and FOXA3. The transfected cells were cultured in ReproFF, L15, WE, or DF12 for seven days. RNA was isolated and subjected to qPCR for determination of AFP (FIG. 2A) and albumin (FIG. 2B) levels. FIGS. 2A and 2B depict the results of transfection with transcription factors and culture in four media. 201B7 cells were transfected with CCAAT/enhancer binding protein alpha (CEBPA) (a), CCAAT/enhancer binding protein beta (CEBPB) (b), and a combination of CEBPA, CEBPB, forkhead box A1, and forkhead box A3. The cells were cultured in ReproFF (FF) (Reprocell), Leibovitz-15 (L15) (Life Technologies), Williams' E (WE) (Life Technologies), or Dulbecco's Modified Eagle Medium/Nutrient F-12 Ham (DF12) (Sigma-Aldrich) for seven days. RNA was isolated and subjected to real-time quantitative PCR for analyzing the expression of alpha-feto protein (A) and albumin (B).

The combination of all four transcription factors and culture in WE yielded the highest expression of AFP and albumin. These results indicated that this condition was suitable for hepatocyte differentiation of iPS cells.

Example 3

This example examines the suitability of various growth media for obtaining enough cells after transfection. 201B7 cells were transfected with the combination of CEBPA, CEBPB, FOXA1, and FOXA3. The transfected cells were cultured in ReproFF (FIG. 3A), L15 (FIG. 3B), WE (FIG. 3C), or DF12 (FIG. 3D) for seven days. Cell survival was less in L15 than in ReproFF, WE, and DF12. FIGS. 3A-3D depict the results of 201B7 cells transfected with four transcription factors and cultured in four media. 201B7 cells were transfected with CCAAT/enhancer binding protein alpha, CCAAT/enhancer binding protein beta, forkhead box 1A, and forkhead box 3A. After transfection, they were cultured in ReproFF (Reprocell) (FIG. 3A), Leibovitz-15 (Life Technologies) (FIG. 3B), Williams' E (Life Technologies) (FIG. 3C), or Dulbecco's Modified Eagle Medium/Nutrient F-12 Ham (DF12) (Sigma-Aldrich) (FIG. 3D) for seven days. The cells were then observed under a microscope. Original magnification: ×200, scale bar: 200 µm. These results indicated that L15 was not suitable to obtain enough cells after transfection.

Example 4

This example examines whether 201B7 cells expressed the transfected genes. FIGS. 4A-4H depicts the results of transfection using CherryPicker1. 201B7 cells were transfected with pEBNK-Hyg/Cherry and cultured in ReproFF (Reprocell) (FIGS. 4A, 4B), Leibovitz-15 (Life Technologies) (FIGS. 4C, 4D), Williams' E (Life Technologies) (FIGS. 4E, 4F), or Dulbecco's Modified Eagle Medium/Nutrient F-12 Ham (DF12) (Sigma-Aldrich) (FIGS. 4G, 4H) for seven days. Cells were then observed with a microscope under white light (FIGS. 4A, 4C, 4E, 4G) or a fluoroscope (FIGS. 4B, 4D, 4F, 4H). Original magnification: ×200, scale bar: 200 µm Fewer cells survived in L15 than in the other three media, which was consistent with the findings in FIGS. 3A-3D. The fluorescence intensity of CherryPicker1 was stronger in 210B7 cells cultured in ReproFF or WE [Tomizawa et al., 2014]. These results indicated that 201B7 cells expressed the transfected gene in ReproFF or WE.

Example 5

Figure 5A:
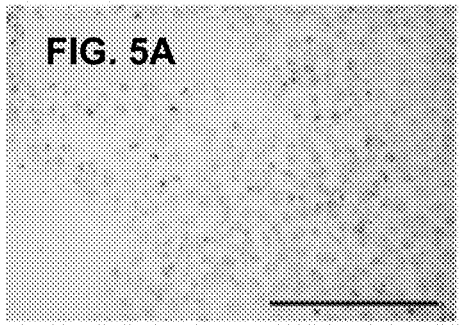
FIGS. 5A-5H are magnified images of 201B7 cells transfected with no plasmids or a combination of plasmids and cultured in various media, immunostained with antibodies against alpha-feto protein (FIGS. 5A, 5B, 5C, and 5D) or albumin (FIGS. 5E, 5F, 5G, and 5H).
Figure 5B:
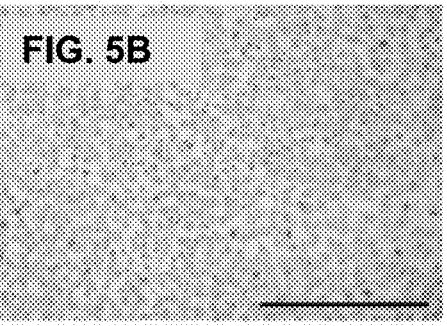
Figure 5C:
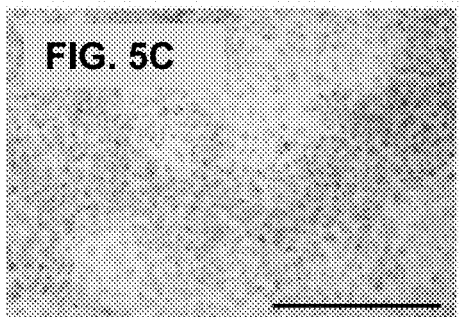
Figure 5D:
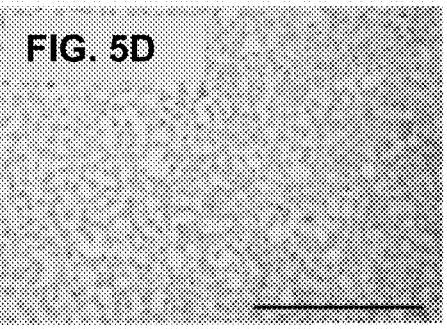
Figure 5E:
Figure 5F:
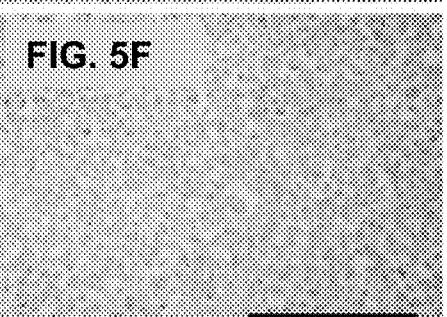
Figure 5G:
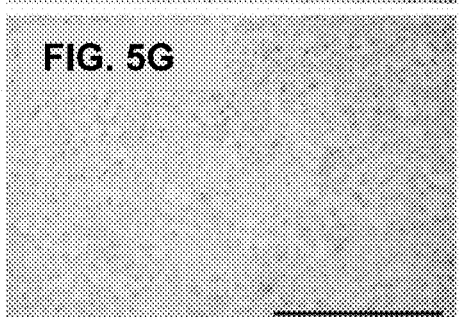
Figure 5H:
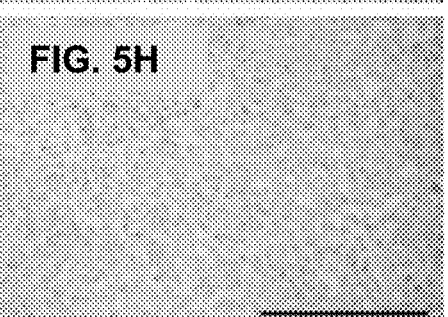

The above results showed that WE was the most suitable medium for culturing 201B7 cells after transfection with transcription factors. To confirm the expression of AFP (FIGS. 5A, 5B, 5C, and 5D) and albumin (FIGS. 5E, 5F, 5G, and 5H) at protein levels, immunostaining was performed after transfection with CEBPA (FIGS. 5B, 5F), CEBPB (FIGS. 5C, 5G), or the combination of CEBPA, CEBPB, FOXA1, and FOXA3 (FIGS. 5D, 5H). AFP and albumin signals were stronger in 201B7 cells transfected with CEBPA, CEBPB, or the combination of CEBPA, CEBPB, FOXA1, and FOXA3 than in untransfected cells (FIGS. 5A, 5E).

Immunostaining was performed as follows. 201B7 cells were transfected with 0.16 µg/well episomal plasmids. The transfected cells were cultured in WE for seven days. After incubation, the cells were fixed with 4% paraformaldehyde (Sigma-Aldrich) at 4° C. for 10 min. The fixed cells were incubated with 0.1% hydrogen peroxide (Wako Pure Chemicals) in 100% methanol (Wako Pure Chemicals) at 4° C. for 30 min to inactivate endogenous peroxide. After rinsing with phosphate-buffered saline (PBS), the specimens were incubated with the wash buffer (2% fetal bovine serum in PBS) at 4° C. for 30 min. Monoclonal anti-human alpha-feto protein (AFP) antibody raised in mouse (Takara) or polyclonal anti-human albumin antibody raised in rabbit (Sigma-Aldrich) was applied to the specimens in wash buffer at 1:1000 dilution. The applied specimens were incubated at 4° C. overnight. After the overnight incubation, the specimens were washed with PBS. After washing, the specimens were incubated with alkaline phosphatase-linked anti-mouse antibody raised in goat (Promega) (Madison, Wis., USA) or alkaline phosphatase-linked anti-rabbit antibody raised in goat (Promega) in wash buffer at 1:1000 dilution at 4° C. for 2 h. After washing with PBS, the conjugates were visualized using Vector Red Substrate (Vector Laboratories) (Burlingame, Calif., USA) according to the manufacturer's instructions. The specimens were observed under a microscope (AX80) (Olympus, Tokyo, Japan).

FIGS. 5A-5H show the results of the immunostaining. 201B7 cells were transfected with no plasmids (FIGS. 5A, 5E), CCAAT/enhancer binding protein alpha (CEBPA) (FIGS. 5B, 5F), CEBPA and CCAAT/enhancer binding protein beta (CEBPB) (FIGS. 5C, 5G), and a combination of CEBPA, CEBPB, forkhead box 1A, and forkhead box 3A (FIGS. 5D, 5H). After seven days of culture in ReproFF (Reprocell), Leibovitz-15 (Life Technologies), Williams' E (Life Technologies), or Dulbecco's Modified Eagle Medium/Nutrient F-12 Ham (DF12) (Sigma-Aldrich) (FIGS. 5D, 5H), the cells were subjected to immunostaining with antibodies against alpha-feto protein (FIGS. 5A, 5B, 5C, 5D) or albumin (FIGS. 5E, 5F, 5G, 5H). Original magnification: ×400, scale bar: 100 µm. These results were consistent with those in FIGS. 2A and 2B.

The present invention includes the following aspects/embodiments/features in any order and/or in any combination:

1. A method of producing hepatocyte lineage cells, comprising:

transfecting a cell with a first expression vector comprising a first gene that encodes CCAAT/enhancer binding protein alpha (CEBPA), a second expression vector comprising a second gene that encodes CCAAT/enhancer binding protein beta (CEBPB), a third expression vector comprising a third gene that encodes forkhead box A1 (FOXA1), and a fourth expression vector comprising a fourth gene that encodes forkhead box A3 (FOXA3); and culturing the transfected cell obtained in a growth environment.

2. The method of any preceding or following embodiment/feature/aspect, further comprising differentiating the transfected cell into a hepatocyte lineage cell.

3. The method of any preceding or following embodiment/feature/aspect, wherein the culturing results in the differentiation of the transfected cell into a hepatocyte lineage cell.

4. The method of any preceding or following embodiment/feature/aspect, wherein the four genes act synergistically to differentiate the cell into a hepatocyte lineage cell.

5. The method of any preceding or following embodiment/feature/aspect, further comprising obtaining a hepatocyte lineage cell from the transfected cell.

6. The method of any preceding or following embodiment/feature/aspect, wherein the hepatocyte lineage cell is an immortal hepatocyte lineage cell.

7. The method of any preceding or following embodiment/feature/aspect, wherein the hepatocyte lineage cell expresses at least one cell surface marker characteristic of hepatocytes.

8. The method of any preceding or following embodiment/feature/aspect, wherein the hepatocyte lineage cell expresses alpha-feto protein, albumin, or both.

9. The method of any preceding or following embodiment/feature/aspect, wherein the transfected cell is cultured in a medium formulated for hepatocyte differentiation, hepatocyte growth, or both.

10. The method of any preceding or following embodiment/feature/aspect, wherein the transfected cell is cultured in Williams' E medium, ReproFF (feeder-free media maintaining pluripotency) medium, or both.

11. The method of any preceding or following embodiment/feature/aspect, wherein the Williams' E medium includes one or more of sodium bicarbonate, L-glutamine, phenol red, and 4-(2-hydroxyethyl)-1-piperazineethanesulfonic acid (HEPES) buffer.

12. The method of any preceding or following embodiment/feature/aspect, wherein the Williams' E medium excludes one or more of sodium bicarbonate, L-glutamine, phenol red, and 4-(2-hydroxyethyl)-1-piperazineethanesulfonic acid (HEPES) buffer.

13. The method of any preceding or following embodiment/feature/aspect, wherein the Williams' E medium is supplemented with fetal bovine serum (FBS).

14. The method of any preceding or following embodiment/feature/aspect, wherein the transfected cell is cultured in Williams' E medium in the growth environment.

15. The method of any preceding or following embodiment/feature/aspect, wherein the transfected cell is cultured in Williams' E medium after culturing in the growth environment.

16. The method of any preceding or following embodiment/feature/aspect, wherein the transfected cell is cultured for from about 4 days to about 12 days.

17. The method of any preceding or following embodiment/feature/aspect, wherein the transfected cell is cultured for at least 7 days.

18. The method of any preceding or following embodiment/feature/aspect, wherein the cell is a mammalian cell.

19. The method of any preceding or following embodiment/feature/aspect, wherein the cell is a human cell.

20. The method of any preceding or following embodiment/feature/aspect, wherein the cell is a stem cell.

21. The method of any preceding or following embodiment/feature/aspect, wherein the cell is a pluripotent stem cell.

22. The method of any preceding or following embodiment/feature/aspect, wherein the cell is an induced pluripotent stem (iPS) cell.

23. The method of any preceding or following embodiment/feature/aspect, wherein the cell is a 201B7 iPS cell.

24. The method of any preceding or following embodiment/feature/aspect, wherein the cell is an embryonic stem cell.

25. The method of any preceding or following embodiment/feature/aspect, wherein the cell is a somatic cell.

26. The method of any preceding or following embodiment/feature/aspect, wherein the cell is a fibroblast.

27. The method of any preceding or following embodiment/feature/aspect, wherein the transfection is performed in vitro.

28. The method of any preceding or following embodiment/feature/aspect, wherein the culturing is performed in vitro.

29. The method of any preceding or following embodiment/feature/aspect, wherein the growth environment is an in vitro growth environment.

30. The method of any preceding or following embodiment/feature/aspect, wherein the growth environment comprises a liquid medium, a solid support, or both.

31. The method of any preceding or following embodiment/feature/aspect, wherein the cell is transfected with the expression vectors simultaneously.

32. The method of any preceding or following embodiment/feature/aspect, wherein the cell is transfected with the expression vectors sequentially.

33. The method of any preceding or following embodiment/feature/aspect, wherein the cell is transfected with at least two of the expression vectors simultaneously.

34. The method of any preceding or following embodiment/feature/aspect, wherein there is a delay of at least 30 minutes between introduction of two or more of the expression vectors.

35. The method of any preceding or following embodiment/feature/aspect, wherein at least one of the genes is constitutively activated.

36. The method of any preceding or following embodiment/feature/aspect, wherein at least one of the genes is inducible.

37. The method of any preceding or following embodiment/feature/aspect, wherein at least one inducible gene is inducible by growth in a suitable medium.

38. The method of any preceding or following embodiment/feature/aspect, wherein the medium is Williams' E medium.

39. The method of any preceding or following embodiment/feature/aspect, wherein the transfection is transient with respect to at least one transcription factor or gene.

40. The method of any preceding or following embodiment/feature/aspect, wherein the transfection is stable with respect to at least one expression factor or gene.

41. A hepatocyte lineage cell obtained by the method of any one of any preceding or following embodiment/feature/aspect.

42. A method of producing hepatocyte lineage cells, comprising the steps of:
(a) introducing four expression vectors into induced pluripotent stem (iPS) cells, wherein the expression vectors are an expression vector containing a gene that encodes CCAAT/enhancer binding protein alpha (CEBPA), an expression vector containing a gene that encodes CCAAT/enhancer binding protein beta (CEBPB), an expression vector containing a gene that encodes forkhead box A1 (FOXA1), and an expression vector containing a gene that encodes forkhead box A3 (FOXA3), and
(b) culturing the cells obtained in step (a) in a growth environment.

43. The method of any preceding or following embodiment/feature/aspect, wherein the cells obtained in step (a) are cultured in Williams' E medium.

44. The method of any preceding or following embodiment/feature/aspect, wherein the cells obtained in step (a) and (b) are cultured in Williams' E medium.

45. The method of any preceding or following embodiment/feature/aspect, wherein the cells obtained in step (a) are cultured for at least seven days.

The present invention can include any combination of these various features or embodiments above and/or below as set forth in sentences and/or paragraphs. Any combination of disclosed features herein is considered part of the present invention and no limitation is intended with respect to combinable features.

Acknowledgements

IRCB003O22, IRAK047019, IRAK015C16, Are07G01, IRAL031O05, IRAK048J15, IRAK0127I02, IRAL058N22, and W01A073N10 were provided by the RIKEN BRC through the National Bio-Resource Project of the MEXT, Japan. This study was supported by a Grant-in-Aid for Scientific Research (C) from Japan Society for the Promotion of Science (JSPS) (15K09032)

The following references are incorporated by reference herein in their entireties.

Akira S, Isshiki H, Sugita T, Tanabe O, Kinoshita S, Nishio Y, Nakajima T, Hirano T, Kishimoto T. 1990. A nuclear factor for IL-6 expression (NF-IL6) is a member of a C/EBP family. Embo J 9:1897-906.

Antonson P, Xanthopoulos K G. 1995. Molecular cloning, sequence, and expression patterns of the human gene encoding CCAAT/enhancer binding protein alpha (C/EBP alpha). Biochem Biophys Res Commun 215:106-13.

Chang H M, Liao Y W, Chiang C H, Chen Y J, Lai Y H, Chang Y L, Chen H L, Jeng S Y, Hsieh J H, Peng C H, Li H Y, Chien Y, Chen S Y, Chen L K, Huo T I. 2012. Improvement of Carbon Tetrachloride-Induced Acute Hepatic Failure by Transplantation of Induced Pluripotent Stem Cells without Reprogramming Factor c-Myc. Int J Mol Sci 13:3598-617.

Costa R H, Kalinichenko V V, Holterman A X, Wang X. 2003. Transcription factors in liver development, differentiation, and regeneration. Hepatology 38:1331-47.

Dabos K J, Nelson L J, Hewage C H, Parkinson J A, Howie A F, Sadler I H, Hayes P C, Plevris J N. 2004. Comparison of bioenergetic activity of primary porcine hepatocytes cultured in four different media. Cell Transplant 13:213-29.

DeLaForest A, Nagaoka M, Si-Tayeb K, Noto F K, Konopka G, Battle M A, Duncan S A. 2011. HNF4A is essential for specification of hepatic progenitors from human pluripotent stem cells. Development 138:4143-53.

Duan Y, Ma X, Zou W, Wang C, Bahbahan I S, Ahuja T P, Tolstikov V, Zem M A. 2010. Differentiation and characterization of metabolically functioning hepatocytes from human embryonic stem cells. Stem Cells 28:674-86.

Farghali H, Lincova D, Gaier N, Kmoniekova E, Kamenikova L, Canova N, Vitek L. 2002. Urea synthesis and cyclosporin a biotransformation in a laboratory scale hepatocyte bioreactor model. Pharmacol Res 46:511-7.

Hang H, Yu Y, Wu N, Huang Q, Xia Q, Bian J. 2014. Induction of highly functional hepatocytes from human umbilical cord mesenchymal stem cells by HNF4alpha transduction. PLoS One 9:e104133.

Hirschi K K, Li S, Roy K. 2014. Induced pluripotent stem cells for regenerative medicine. Annu Rev Biomed Eng 16:277-94.

Inamura M, Kawabata K, Takayama K, Tashiro K, Sakurai F, Katayama K, Toyoda M, Akutsu H, Miyagawa Y, Okita H, Kiyokawa N, Umezawa A, Hayakawa T, Furue MK, Mizuguchi H. 2010. Efficient Generation of Hepatoblasts From Human ES Cells and iPS Cells by Transient Overexpression of Homeobox Gene HEX. Mol Ther. 19(2):400-7.

Kheolamai P, Dickson A J. 2009. Liver-enriched transcription factors are critical for the expression of hepatocyte marker genes in mES-derived hepatocyte-lineage cells. BMC Mol Biol 10:35.

Mitaka T, Sattler C A, Sattler G L, Sargent L M, Pitot H C. 1991. Multiple cell cycles occur in rat hepatocytes cultured in the presence of nicotinamide and epidermal growth factor. Hepatology 13:21-30.

Miyanari Y, Torres-Padilla M E. 2012. Control of ground-state pluripotency by allelic regulation of Nanog. Nature 483:470-3.

Nakamura T, Teramoto H, Tomita Y, Ichihara A. 1984. L-proline is an essential amino acid for hepatocyte growth in culture. Biochem Biophys Res Commun 122:884-91.

Pretlow T G, 2nd, Williams E E. 1973. Separation of hepatocytes from suspensions of mouse liver cells using programmed gradient sedimentation in gradients of ficoll in tissue sulture medium. Anal Biochem 55:114-22.

Shibata M A, Miwa Y, Morimoto J, Otsuki Y. 2007. Easy stable transfection of a human cancer cell line by electrogene transfer with an Epstein-Barr virus-based plasmid vector. Med Mol Morphol 40:103-7.

Si-Tayeb K, Noto F K, Nagaoka M, Li J, Battle M A, Duris C, North P E, Dalton S, Duncan S A. 2010. Highly efficient generation of human hepatocyte-like cells from induced pluripotent stem cells. Hepatology 51:297-305.

Simeonov K P, Uppal H. 2014. Direct reprogramming of human fibroblasts to hepatocyte-like cells by synthetic modified mRNAs. PLoS One 9:e100134.

Song Z, Cai J, Liu Y, Zhao D, Yong J, Duo S, Song X, Guo Y, Zhao Y, Qin H, Yin X, Wu C, Che J, Lu S, Ding M, Deng H. 2009. Efficient generation of hepatocyte-like cells from human induced pluripotent stem cells. Cell Res 19:1233-42.

Takahashi K, Tanabe K, Ohnuki M, Narita M, Ichisaka T, Tomoda K, Yamanaka S. 2007. Induction of pluripotent stem cells from adult human fibroblasts by defined factors. Cell 131:861-72.

Takayama K, Inamura M, Kawabata K, Katayama K, Higuchi M, Tashiro K, Nonaka A, Sakurai F, Hayakawa T, Kusuda Fume M, Mizuguchi H. 2012. Efficient Generation of Functional Hepatocytes From Human Embryonic Stem Cells and Induced Pluripotent Stem Cells by HNF4alpha Transduction. Mol Ther 20:127-37.

Takeba Y, Matsumoto N, Takenoshita-Nakaya S, Harimoto Y, Kumai T, Kinoshita Y, Nakano H, Ohtsubo T, Kobayashi S. 2011. Comparative study of culture conditions for maintaining CYP3A4 and ATP-binding cassette transporters activity in primary cultured human hepatocytes. J Pharmacol Sci 115:516-24.

Takebe T, Sekine K, Enomura M, Koike H, Kimura M, Ogaeri T, Zhang RR, Ueno Y, Zheng Y W, Koike N, Aoyama S, Adachi Y, Taniguchi H. 2013. Vascularized and functional human liver from an iPSC-derived organ bud transplant. Nature 499:481-4.

Tanaka J, Miwa Y, Miyoshi K, Ueno A, Inoue H. 1999. Construction of Epstein-Barr virus-based expression vector containing mini-oriP. Biochem Biophys Res Commun 264:938-43.

Tomizawa M, Garfield S, Factor V, Xanthopoulos K G. 1998. Hepatocytes deficient in CCAAT/enhancer binding protein alpha (C/EBP alpha) exhibit both hepatocyte and biliary epithelial cell character. Biochem Biophys Res Commun 249:1-5.

Tomizawa M, Shinozaki F, Motoyoshi Y, Sugiyama T, Yamamoto S, Ishige N. 2015. An Optimal Medium Supplementation Regimen for Initiation of Hepatocyte Differentiation in Human Induced Pluripotent Stem Cells. J Cell Biochem 116:1479-89.

Tomizawa M, Shinozaki F, Motoyoshi Y, Sugiyama T, Yamamoto S, Sueishi M. 2014. Dual gene expression in embryoid bodies derived from human induced pluripotent stem cells using episomal vectors. Tissue Eng Part A 20:3154-62.

Tomizawa M, Shinozaki F, Sugiyama T, Yamamoto S, Sueishi M, Yoshida T. 2013. Single-step protocol for the differentiation of human-induced pluripotent stem cells into hepatic progenitor-like cells. Biomed Rep 1:18-22.

Tomizawa M, Shinozaki F, Motoyoshi Y, Sugiyama T, Yamamoto S, Ishige N. Jan. 15, 2016. Transcription factors and medium suitable for initiating the differentiation of human induced pluripotent stem cells to the hepatocyte lineage. J Cell Biochem, 10.1002/jcb.25494.

van Wenum M, Chamuleau R A, van Gulik T M, Siliakus A, Seppen J, Hoekstra R. 2014. Bioartificial livers in vitro and in vivo: tailoring biocomponents to the expanding variety of applications. Expert Opin Biol Ther 14:1745-60.

Wu D, Ramin S A, Cederbaum A I. 1997. Effect of pyridine on the expression of cytochrome P450 isozymes in primary rat hepatocyte culture. Mol Cell Biochem 173:103-11.

Xu C R, Zaret K S. 2012. Chromatin "pre-pattern" and epigenetic modulation in the cell fate choice of liver over pancreas in the endoderm. Nucleus 3:150-4.

Yamasaki H, Sada A, Iwata T, Niwa T, Tomizawa M, Xanthopoulos K G, Koike T, Shiojiri N. 2006. Suppression of C/EBPalpha expression in periportal hepatoblasts may stimulate biliary cell differentiation through increased Hnf6 and Hnf1b expression. Development 133:4233-43.

Yates J L, Warren N, Sugden B. 1985. Stable replication of plasmids derived from Epstein-Barr virus in various mammalian cells. Nature 313:812-5.

Zaret K S, Carroll J S. 2011. Pioneer transcription factors: establishing competence for gene expression. Genes Dev 25:2227-41.

Zaret K S, Watts J, Xu J, Wandzioch E, Smale S T, Sekiya T. 2008. Pioneer factors, genetic competence, and inductive signaling: programming liver and pancreas progenitors from the endoderm. Cold Spring Harb Symp Quant Biol 73:119-26.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method of producing hepatocyte cells, comprising:
transfecting a cell with a first expression vector comprising a first gene that encodes CCAAT/enhancer binding protein alpha (CEBPA), a second expression vector comprising a second gene that encodes CCAAT/enhancer binding protein beta (CEBPB), a third expression vector comprising a third gene that encodes forkhead box A1 (FOXA1), and a fourth expression vector comprising a fourth gene that encodes forkhead box A3 (FOXA3); and
culturing the transfected cell obtained in a growth environment.

2. The method of claim 1, further comprising differentiating the transfected cell into a hepatocyte cell.

3. The method of claim 1, wherein the culturing results in the differentiation of the transfected cell into a hepatocyte cell.

4. The method of claim 1, wherein the four genes act synergistically to differentiate the cell into a hepatocyte cell.

5. The method of claim 1, further comprising obtaining a hepatocyte cell from the transfected cell.

6. The method of claim 5, wherein the hepatocyte cell is an immortal hepatocyte cell.

7. The method of claim 5, wherein the hepatocyte cell expresses at least one cell surface marker.

8. The method of claim 5, wherein the hepatocyte cell expresses alpha-feto protein, albumin, or both.

9. The method of claim 1, wherein the transfected cell is cultured in a medium formulated for hepatocyte differentiation, hepatocyte growth, or both.

10. The method of claim 1, wherein the transfected cell is cultured in Williams' E medium, ReproFF medium, or both.

11. The method of claim 10, wherein the Williams' E medium includes one or more of sodium bicarbonate, L-glutamine, phenol red, and 4-(2-hydroxyethyl)-1-piperazineethanesulfonic acid (HEPES) buffer.

12. The method of claim 10, wherein the Williams' E medium excludes one or more of sodium bicarbonate, L-glutamine, phenol red, and 4-(2-hydroxyethyl)-1-piperazineethanesulfonic acid (HEPES) buffer.

13. The method of claim 10, wherein the Williams' E medium is supplemented with fetal bovine serum (FBS).

14. The method of claim 1, wherein the transfected cell is cultured in Williams' E medium in the growth environment.

15. The method of claim 1, wherein the transfected cell is cultured in Williams' E medium after culturing in the growth environment.

16. The method of claim 1, wherein the transfected cell is cultured for from about 4 days to about 12 days.

17. The method of claim 1, wherein the transfected cell is cultured for at least 7 days.

18. The method of claim 1, wherein the cell is a mammalian cell.

19. The method of claim 1, wherein the cell is a human cell.

20. The method of claim 1, wherein the cell is a stem cell.

21. The method of claim 1, wherein the cell is a pluripotent stem cell.

22. The method of claim 1, wherein the cell is an induced pluripotent stem (iPS) cell.

23. The method of claim 1, wherein the cell is a 201B7 iPS cell.

24. The method of claim 1, wherein the cell is an embryonic stem cell.

25. The method of claim 1, wherein the cell is a somatic cell.

26. The method of claim 1, wherein the cell is a fibroblast.

27. The method of claim 1, wherein the transfection is performed in vitro.

28. The method of claim 1, wherein the growth environment comprises a liquid medium, a solid support, or both.

29. The method of claim 1, wherein the cell is transfected with the expression vectors simultaneously.

30. The method of claim 1, wherein the cell is transfected with the expression vectors sequentially.

31. The method of claim 1, wherein the cell is transfected with at least two of the expression vectors simultaneously.

32. The method of claim 1, wherein there is a delay of at least 30 minutes between introduction of two or more of the expression vectors.

33. The method of claim 1, wherein at least one of the genes is constitutively activated.

34. The method of claim 1, wherein at least one of the genes is inducible.

35. The method of claim 34, wherein at least one inducible gene is inducible by growth in a growth medium.

36. The method of claim 35, wherein the medium is Williams' E medium.

37. The method of claim 1, wherein the transfection is transient with respect to a transcription factor or gene.

38. The method of claim 1, wherein the transfection is stable with respect to at least one expression vector or gene.

39. A hepatocyte cell obtained by the method of claim 1, wherein the hepatocyte cell comprises said first expression vector, said second expression vector, said third expression vector, and said fourth expression vector.

40. A method of producing hepatocyte cells, comprising the steps of:
  (a) introducing four expression vectors into induced pluripotent stem (iPS) cells, wherein the expression vectors are an expression vector containing a gene that encodes CCAAT/enhancer binding protein alpha (CEBPA), an expression vector containing a gene that encodes CCAAT/enhancer binding protein beta (CEBPB), an expression vector containing a gene that encodes forkhead box A1 (FOXA1), and an expression vector containing a gene that encodes forkhead box A3 (FOXA3), and
  (b) culturing the cells obtained in step (a) in a growth environment.

41. The method of claim 40, wherein the cells obtained in step (a) are cultured in Williams' E medium.

42. The method of claim 40, wherein the cells obtained in step (a) and (b) are cultured in Williams' E medium.

43. The method of claim 40, wherein the cells obtained in step (a) are cultured for at least seven days.

* * * * *

SEQUENCE LISTING

<160> NUMBER OF SEQ ID NOS: 46

<210> SEQ ID NO 1
<211> LENGTH: 30
<212> TYPE: DNA
<213> ORGANISM: Artificial
<220> FEATURE:
<223> OTHER INFORMATION: primer

<400> SEQUENCE: 1
atcgtctaga atggagaaaa tgtcccgacc                                        30

<210> SEQ ID NO 2
<211> LENGTH: 30
<212> TYPE: DNA
<213> ORGANISM: Artificial
<220> FEATURE:
<223> OTHER INFORMATION: primer

<400> SEQUENCE: 2
atcgggtacc ctacaggggc ccgtgcctgg                                        30

<210> SEQ ID NO 3
<211> LENGTH: 30
<212> TYPE: DNA
<213> ORGANISM: Artificial
<220> FEATURE:
<223> OTHER INFORMATION: primer

<400> SEQUENCE: 3
atcgtctaga atggtgtcca agctcacgtc                                        30

<210> SEQ ID NO 4
<211> LENGTH: 30
<212> TYPE: DNA
<213> ORGANISM: Artificial
<220> FEATURE:
<223> OTHER INFORMATION: primer

<400> SEQUENCE: 4
atcgggtacc tcaccaggct tgtagaggac                                        30

<210> SEQ ID NO 5
<211> LENGTH: 30
<212> TYPE: DNA
<213> ORGANISM: Artificial
<220> FEATURE:
<223> OTHER INFORMATION: primer

<400> SEQUENCE: 5
atcgtctaga atgagcagcc cggatgcggg                                                30

<210> SEQ ID NO 6
<211> LENGTH: 30
<212> TYPE: DNA
<213> ORGANISM: Artificial
<220> FEATURE:
<223> OTHER INFORMATION: primer

<400> SEQUENCE: 6
atcgggtacc tcacacgtca ggatagttgc                                                30

<210> SEQ ID NO 7
<211> LENGTH: 22
<212> TYPE: DNA
<213> ORGANISM: Artificial
<220> FEATURE:
<223> OTHER INFORMATION: primer

<400> SEQUENCE: 7
cggacttggt gcgtctaaga tg                                                        22

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
gcattggagc ggtgagtttg                                                           20

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
aagcacagcg acgagtacaa                                                           20

<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10
agctgctcca ccttcttctg                                                           20

<210> SEQ ID NO 11
<211> LENGTH: 20
<212> TYPE: DNA
<213> ORGANISM: Artificial
<220> FEATURE:

<223> OTHER INFORMATION: primer

<400> SEQUENCE: 11
agaagttggt ggagctgtcg                                               20

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
cagctgcttg aagaactgcc                                               20

<210> SEQ ID NO 13
<211> LENGTH: 23
<212> TYPE: DNA
<213> ORGANISM: Artificial
<220> FEATURE:
<223> OTHER INFORMATION: primer

<400> SEQUENCE: 13
ggacttcaag gcatacgaac agg                                           23

<210> SEQ ID NO 14
<211> LENGTH: 24
<212> TYPE: DNA
<213> ORGANISM: Artificial
<220> FEATURE:
<223> OTHER INFORMATION: primer

<400> SEQUENCE: 14
taggacgggt ctggaataca cacc                                          24

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
gatacctcct actaccaggg                                               20

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
cacttgctct ctcacttgtc                                               20

<210> SEQ ID NO 17
<211> LENGTH: 22
<212> TYPE: DNA
<213> ORGANISM: Artificial
<220> FEATURE:
<223> OTHER INFORMATION: primer

<400> SEQUENCE: 17
aaggagatgc cgaagggta tc                                             22

```
<210> SEQ ID NO 18
<211> LENGTH: 25
<212> TYPE: DNA
<213> ORGANISM: Artificial
<220> FEATURE:
<223> OTHER INFORMATION: primer

<400> SEQUENCE: 18
ctggtagatt tcactcaagg tcagc                                              25

<210> SEQ ID NO 19
<211> LENGTH: 22
<212> TYPE: DNA
<213> ORGANISM: Artificial
<220> FEATURE:
<223> OTHER INFORMATION: primer

<400> SEQUENCE: 19
tctcagtcag tgcgatgtct gg                                                 22

<210> SEQ ID NO 20
<211> LENGTH: 23
<212> TYPE: DNA
<213> ORGANISM: Artificial
<220> FEATURE:
<223> OTHER INFORMATION: primer

<400> SEQUENCE: 20
aggagggaag agggaagatt acg                                                23

<210> SEQ ID NO 21
<211> LENGTH: 22
<212> TYPE: DNA
<213> ORGANISM: Artificial
<220> FEATURE:
<223> OTHER INFORMATION: primer

<400> SEQUENCE: 21
ccactcgtgt ctgcttttgt gc                                                 22

<210> SEQ ID NO 22
<211> LENGTH: 24
<212> TYPE: DNA
<213> ORGANISM: Artificial
<220> FEATURE:
<223> OTHER INFORMATION: primer

<400> SEQUENCE: 22
cccttccctt ccatcttctc tcac                                               24

<210> SEQ ID NO 23
<211> LENGTH: 24
<212> TYPE: DNA
<213> ORGANISM: Artificial
<220> FEATURE:
<223> OTHER INFORMATION: primer

<400> SEQUENCE: 23
gcccagtgaa cagaataaag gtgc                                               24

<210> SEQ ID NO 24
<211> LENGTH: 22
<212> TYPE: DNA
<213> ORGANISM: Artificial
<220> FEATURE:
<223> OTHER INFORMATION: primer
```

```
<400> SEQUENCE: 24
ccaatgccag tggtcatcat cc                                          22

<210> SEQ ID NO 25
<211> LENGTH: 21
<212> TYPE: DNA
<213> ORGANISM: Artificial
<220> FEATURE:
<223> OTHER INFORMATION: primer

<400> SEQUENCE: 25
tcgtcaatcc atcagcaatg c                                           21

<210> SEQ ID NO 26
<211> LENGTH: 22
<212> TYPE: DNA
<213> ORGANISM: Artificial
<220> FEATURE:
<223> OTHER INFORMATION: primer

<400> SEQUENCE: 26
tccaatacac ccccatctct tg                                          22

<210> SEQ ID NO 27
<211> LENGTH: 20
<212> TYPE: DNA
<213> ORGANISM: Artificial
<220> FEATURE:
<223> OTHER INFORMATION: primer

<400> SEQUENCE: 27
acctgtccca acacctcaac                                             20

<210> SEQ ID NO 28
<211> LENGTH: 20
<212> TYPE: DNA
<213> ORGANISM: Artificial
<220> FEATURE:
<223> OTHER INFORMATION: primer

<400> SEQUENCE: 28
ctcatcacct gtgggctctt                                             20

<210> SEQ ID NO 29
<211> LENGTH: 22
<212> TYPE: DNA
<213> ORGANISM: Artificial
<220> FEATURE:
<223> OTHER INFORMATION: primer

<400> SEQUENCE: 29
aaagaacccc agcaaggaag ag                                          22

<210> SEQ ID NO 30
<211> LENGTH: 22
<212> TYPE: DNA
<213> ORGANISM: Artificial
<220> FEATURE:
<223> OTHER INFORMATION: primer

<400> SEQUENCE: 30
acggacctca gtgaccaagt tg                                          22

<210> SEQ ID NO 31
<211> LENGTH: 24
```

```
<212> TYPE: DNA
<213> ORGANISM: Artificial
<220> FEATURE:
<223> OTHER INFORMATION: primer

<400> SEQUENCE: 31
acctcatcct ccttcttcag ggac                                           24

<210> SEQ ID NO 32
<211> LENGTH: 24
<212> TYPE: DNA
<213> ORGANISM: Artificial
<220> FEATURE:
<223> OTHER INFORMATION: primer

<400> SEQUENCE: 32
gcttttcctc tccactccaa gttc                                           24

<210> SEQ ID NO 33
<211> LENGTH: 19
<212> TYPE: DNA
<213> ORGANISM: Artificial
<220> FEATURE:
<223> OTHER INFORMATION: primer

<400> SEQUENCE: 33
tcagtcattt cacaccagc                                                 19

<210> SEQ ID NO 34
<211> LENGTH: 19
<212> TYPE: DNA
<213> ORGANISM: Artificial
<220> FEATURE:
<223> OTHER INFORMATION: primer

<400> SEQUENCE: 34
tgccaaaagt gctatcctg                                                 19

<210> SEQ ID NO 35
<211> LENGTH: 20
<212> TYPE: DNA
<213> ORGANISM: Artificial
<220> FEATURE:
<223> OTHER INFORMATION: primer

<400> SEQUENCE: 35
actccactcc aacctccaag                                                20

<210> SEQ ID NO 36
<211> LENGTH: 20
<212> TYPE: DNA
<213> ORGANISM: Artificial
<220> FEATURE:
<223> OTHER INFORMATION: primer

<400> SEQUENCE: 36
gtggccagga gtgttcaaat                                                20

<210> SEQ ID NO 37
<211> LENGTH: 26
<212> TYPE: DNA
<213> ORGANISM: Artificial
<220> FEATURE:
<223> OTHER INFORMATION: primer

<400> SEQUENCE: 37
```
cgctttcatg gtgtgggcta aggacg 26

<210> SEQ ID NO 38
<211> LENGTH: 26
<212> TYPE: DNA
<213> ORGANISM: Artificial
<220> FEATURE:
<223> OTHER INFORMATION: primer

<400> SEQUENCE: 38
tagttggggt ggtcctgcat gtgctg 26

<210> SEQ ID NO 39
<211> LENGTH: 20
<212> TYPE: DNA
<213> ORGANISM: Artificial
<220> FEATURE:
<223> OTHER INFORMATION: primer

<400> SEQUENCE: 39
cgaatgccag agaaggtcac 20

<210> SEQ ID NO 40
<211> LENGTH: 20
<212> TYPE: DNA
<213> ORGANISM: Artificial
<220> FEATURE:
<223> OTHER INFORMATION: primer

<400> SEQUENCE: 40
ccatgagaat ccgcttgttt 20

<210> SEQ ID NO 41
<211> LENGTH: 20
<212> TYPE: DNA
<213> ORGANISM: Artificial
<220> FEATURE:
<223> OTHER INFORMATION: primer

<400> SEQUENCE: 41
acacaaaaag cccactccag 20

<210> SEQ ID NO 42
<211> LENGTH: 20
<212> TYPE: DNA
<213> ORGANISM: Artificial
<220> FEATURE:
<223> OTHER INFORMATION: primer

<400> SEQUENCE: 42
ggtgcataca ggaagggatg 20

<210> SEQ ID NO 43
<211> LENGTH: 22
<212> TYPE: DNA
<213> ORGANISM: Artificial
<220> FEATURE:
<223> OTHER INFORMATION: primer

<400> SEQUENCE: 43
gctcgtgaaa cacaagccca ag 22

<210> SEQ ID NO 44
<211> LENGTH: 23
<212> TYPE: DNA
<213> ORGANISM: Artificial

```
<220> FEATURE:
<223> OTHER INFORMATION: primer

<400> SEQUENCE: 44
gcaaagcagg tctccttatc gtc                                          23

<210> SEQ ID NO 45
<211> LENGTH: 20
<212> TYPE: DNA
<213> ORGANISM: Artificial
<220> FEATURE:
<223> OTHER INFORMATION: primer

<400> SEQUENCE: 45 ccgttttttgg ctctgttttg                                             20

<210> SEQ ID NO 46
<211> LENGTH: 20
<212> TYPE: DNA
<213> ORGANISM: Artificial
<220> FEATURE:
<223> OTHER INFORMATION: primer

<400> SEQUENCE: 46
tcatcgaaac actcggtgaa                                              20
```